US007288550B2

(12) United States Patent
Dellaria et al.

(10) Patent No.: US 7,288,550 B2
(45) Date of Patent: Oct. 30, 2007

(54) THIOETHER SUBSTITUTED IMIDAZOQUINOLINES

(75) Inventors: Joseph F. Dellaria, Woodbury, MN (US); Matthew R. Radmer, Robbinsdale, MN (US); Bryon A. Merrill, River Falls, WI (US)

(73) Assignee: 3M Innovative Properties Company, St. Paul, MN (US)

( * ) Notice: Subject to any disclaimer, the term of this patent is extended or adjusted under 35 U.S.C. 154(b) by 188 days.

(21) Appl. No.: 11/132,537

(22) Filed: May 19, 2005

(65) Prior Publication Data

US 2005/0209267 A1 Sep. 22, 2005

Related U.S. Application Data

(60) Division of application No. 10/696,684, filed on Oct. 29, 2003, now Pat. No. 6,921,826, which is a continuation of application No. 10/013,059, filed on Dec. 6, 2001, now Pat. No. 6,664,264.

(60) Provisional application No. 60/254,218, filed on Dec. 8, 2000.

(51) Int. Cl.
A61K 31/4353 (2006.01)
C07D 471/04 (2006.01)
(52) U.S. Cl. ........................ 514/293; 546/82
(58) Field of Classification Search ............... 546/82; 514/293
See application file for complete search history.

(56) References Cited

U.S. PATENT DOCUMENTS

| | | |
|---|---|---|
| 3,314,941 A | 4/1967 | Littell et al. |
| 4,689,338 A | 8/1987 | Gerster |
| 4,698,348 A | 10/1987 | Gerster |
| 4,929,624 A | 5/1990 | Gerster et al. |
| 4,988,815 A | 1/1991 | Andre et al. |
| 5,037,986 A | 8/1991 | Gerster |
| 5,175,296 A | 12/1992 | Gerster |
| 5,238,944 A | 8/1993 | Wick et al. |
| 5,266,575 A | 11/1993 | Gerster |
| 5,268,376 A | 12/1993 | Gester |
| 5,346,905 A | 9/1994 | Gerster |
| 5,352,784 A | 10/1994 | Nikolaides et al. |
| 5,367,076 A | 11/1994 | Gerster |
| 5,389,640 A | 2/1995 | Gerster et al. |
| 5,395,937 A | 3/1995 | Nikolaides et al. |
| 5,446,153 A | 8/1995 | Lindstrom et al. |
| 5,482,936 A | 1/1996 | Lindstrom |
| 5,693,811 A | 12/1997 | Lindstrom |
| 5,741,908 A | 4/1998 | Gerster et al. |
| 5,756,747 A | 5/1998 | Gerster et al. |
| 5,939,090 A | 8/1999 | Beaurline et al. |
| 6,039,969 A | 3/2000 | Tomai et al. |
| 6,069,149 A | 5/2000 | Nanba et al. |
| 6,083,505 A | 7/2000 | Miller et al. |
| 6,110,929 A | 8/2000 | Gerster et al. |
| 6,194,425 B1 | 2/2001 | Gerster et al. |
| 6,245,776 B1 | 6/2001 | Skwierczynski et al. |
| 6,331,539 B1 | 12/2001 | Crooks et al. |
| 6,376,669 B1 | 4/2002 | Rice et al. |
| 6,451,810 B1 | 9/2002 | Coleman et al. |
| 6,518,265 B1 | 2/2003 | Kato et al. |
| 6,525,064 B1 | 2/2003 | Dellaria et al. |
| 6,541,485 B1 | 4/2003 | Crooks et al. |
| 6,545,016 B1 | 4/2003 | Dellaria et al. |
| 6,545,017 B1 | 4/2003 | Dellaria et al. |
| 6,558,951 B1 | 5/2003 | Tomai et al. |
| 6,573,273 B1 | 6/2003 | Crooks et al. |
| 6,656,938 B2 | 12/2003 | Crooks et al. |
| 6,660,735 B2 | 12/2003 | Crooks et al. |
| 6,660,747 B2 | 12/2003 | Crooks et al. |
| 6,664,260 B2 | 12/2003 | Charles et al. |
| 6,664,264 B2 | 12/2003 | Dellaria et al. |
| 6,664,265 B2 | 12/2003 | Crooks et al. |
| 6,667,312 B2 | 12/2003 | Bonk et al. |
| 6,670,372 B2 | 12/2003 | Charles et al. |
| 6,677,347 B2 | 1/2004 | Crooks et al. |
| 6,677,348 B2 | 1/2004 | Heppner et al. |
| 6,677,349 B1 | 1/2004 | Griesgraber |
| 6,683,088 B2 | 1/2004 | Crooks et al. |
| 6,696,465 B2 | 2/2004 | Dellaria, Jr. et al. |
| 6,706,728 B2 | 3/2004 | Hedenstrom et al. |
| 6,743,920 B2 | 6/2004 | Lindstrom et al. |
| 6,756,382 B2 | 6/2004 | Coleman et al. |

(Continued)

FOREIGN PATENT DOCUMENTS

| | | |
|---|---|---|
| EP | 0 394 026 | 10/1990 |
| EP | 1 104 764 | 6/2001 |
| JP | 9-208584 | 8/1997 |
| JP | 9-255926 | 3/1999 |
| JP | 11-222432 | 8/1999 |
| JP | 2000-247884 | 9/2000 |
| WO | WO 01/74343 | 10/2001 |
| WO | WO 02/36592 | 5/2002 |
| WO | WO 02/46749 | 6/2002 |
| WO | WO 02/46194 | 8/2002 |

(Continued)

OTHER PUBLICATIONS

English Abstract AN 125:31527 Ca. Cohen Marion et al 1996, vol. 105 Issue 5, pp. 589-598, Cytokine function:A study in biologic diversity.*

(Continued)

Primary Examiner—Rita Desai
(74) Attorney, Agent, or Firm—Dean A. Ersfeld

(57) ABSTRACT

Imidazoquinoline and tetrahydroimidazoquinoline compounds that contain thioether functionality at the 1-position are useful as immune response modifiers. The compounds and compositions of the invention can induce the biosynthesis of various cytokines and are useful in the treatment of a variety of conditions including viral diseases and neoplastic diseases.

1 Claim, No Drawings

U.S. PATENT DOCUMENTS

| | | |
|---|---|---|
| 6,797,718 B2 | 9/2004 | Dellaria et al. |
| 6,818,650 B2 | 11/2004 | Griesgraber |
| 2002/0016332 A1 | 2/2002 | Slade |
| 2002/0055517 A1 | 5/2002 | Smith |
| 2002/0058674 A1 | 5/2002 | Hedenstrom et al. |
| 2002/0110840 A1 | 8/2002 | Tomai et al. |
| 2003/0130299 A1 | 7/2003 | Crooks et al. |
| 2003/0133913 A1 | 7/2003 | Tomai et al. |
| 2003/0139364 A1 | 7/2003 | Krieg et al. |
| 2003/0161797 A1 | 8/2003 | Miller et al. |
| 2003/0199538 A1 | 10/2003 | Skwierczynski et al. |
| 2004/0014779 A1 | 1/2004 | Gorden et al. |
| 2004/0091491 A1 | 5/2004 | Kedl et al. |
| 2004/0132079 A1 | 7/2004 | Gupta et al. |
| 2004/0141950 A1 | 7/2004 | Noelle et al. |
| 2004/0147543 A1 | 7/2004 | Hays et al. |
| 2004/0162309 A1 | 8/2004 | Gorden et al. |
| 2004/0171086 A1 | 9/2004 | Fink et al. |
| 2004/0175336 A1 | 9/2004 | Egging et al. |
| 2004/0176367 A1 | 9/2004 | Griesgraber et al. |
| 2004/0180919 A1 | 9/2004 | Lee et al. |
| 2004/0181130 A1 | 9/2004 | Fox et al. |
| 2004/0181211 A1 | 9/2004 | Elliott et al. |
| 2004/0191833 A1 | 9/2004 | Fink et al. |
| 2004/0192585 A1 | 9/2004 | Fox et al. |
| 2004/0197865 A1 | 10/2004 | Gupta et al. |
| 2004/0202720 A1 | 10/2004 | Wightman et al. |
| 2005/0054590 A1 | 3/2005 | Averett |

FOREIGN PATENT DOCUMENTS

| | | |
|---|---|---|
| WO | WO 02/102377 | 12/2002 |
| WO | WO 03/020889 | 3/2003 |
| WO | WO 03/043572 | 5/2003 |
| WO | WO 03/045391 | 6/2003 |
| WO | WO 03/097641 | 11/2003 |
| WO | WO 04/091500 | 10/2004 |

OTHER PUBLICATIONS

Wozniak, et al, "The Amination of 3-nitro-1, 5-naphthyridines by Liquid Ammonia/Potassium Permanganate[1,2]. A New and Convenient Amination Method.", *Journal of the Royal Netherlands Chemical Society*, 102, pp. 511-513, Dec. 12, 1983.

Brennan, et al, "Automated Bioassay of Interferons in Micro-test Plates", *Biotechniques*, Jun./Jul. 78, 1983.

Testerman, et al., "Cytokine Induction by the Immunomodulators Imiquimod and S-27609", *Journal of Leukocyte Biology*, vol. 58, pp. 365-372, Sep. 1995.

Bachman, et al, "Synthesis of Substituted Quinolylamines. Derivatives of 4-Amino-7-Chloroquinoline", *J. Org. Chem*, 15, pp. 1278-1284 (1950).

Jain, et al, "Chemical and Pharmacological Investigations of Some ω-Substituted Alkylamino-3-aminopyridines", *J. Med. Chem.*, 11, pp. 87-92 (1968).

Baranov, et al., *Chem. Abs.* 85, 94362, (1976).

Berényi, et al, "Ring Transformation of Condensed Dihydro-astriazines", *J. Heterocyclic Chem.*, 18, pp. 1537-1540 (1981).

Chollet, et al., "Development of a Topically Active Imiquimod Formulation", *Pharmaceutical Development and Technology*, 4(1), pp. 35-43 (1999).

Izumi, et al., "1H-Imidazo[4,5-c]quinoline Derivatives as Novel Potent TNF-α Suppressors: Synthesis and Structure-Activity Relationship of 1-, 2- and 4-Substituted 1H-imidazo[4,5-c]pyridines", *Bioorganic & Medicinal Chemistry*, 11, pp. 2541-2550 (2003).

R.L. Miller et al., "Imiquimod applied topically: a novel immune response modifier and new class of drug", *International Journal of Immunopharmacology*, 21, 1-14 (1999).

Sof'ina et al., "Experimental Evaluation of Antitumor Drugs in the USA and USSR and Clinical Correlations", *NCI Monograph 55*, NIH Publication No. 80-1933, pp. 76-78, (1980).

Strandtmann, *J Med. Chem*, 10(6), pp. 1063-1065 (1967).

Delgado et al., *Wilson and Gisvold's Textboo of Organic Medicianal and Pharmaceutical Chemistry*, 9th Edition, pp. 30-31 (1991).

\* cited by examiner

THIOETHER SUBSTITUTED IMIDAZOQUINOLINES

CROSS REFERENCE TO RELATED APPLICATIONS

This application is a divisional of U.S. application Ser. No. 10/696,684, filed Oct. 29, 2003, now U.S. Pat. No. 6,921,826, which is a continuation of U.S. application Ser. No. 10/013,059, filed Dec. 6, 2001, now U.S. Pat. No. 6,664,264, which claims the benefit of U.S. Provisional Application No. 60/254,218, filed Dec. 8, 2000.

FIELD OF THE INVENTION

This invention relates to imidazoquinoline compounds that have thioether functionality at the 1-position, and to pharmaceutical compositions containing such compounds. A further aspect of this invention relates to the use of these compounds as immunomodulators, for inducing cytokine biosynthesis in animals, and in the treatment of diseases, including viral and neoplastic diseases.

BACKGROUND OF THE INVENTION

The first reliable report on the 1H-imidazo[4,5-c]quinoline ring system, Backman et al., *J. Org. Chem.* 15, 1278–1284 (1950) describes the synthesis of 1-(6-methoxy-8-quinolinyl)-2-methyl-1H-imidazo[4,5-c]quinoline for possible use as an antimalarial agent. Subsequently, syntheses of various substituted 1H-imidazo[4,5-c]quinolines were reported. For example, Jain et al., *J. Med. Chem.* 11, pp. 87–92 (1968), synthesized the compound 1-[2-(4-piperidyl)ethyl]-1H-imidazo[4,5-c]quinoline as a possible anticonvulsant and cardiovascular agent. Also, Baranov et al., *Chem. Abs.* 85, 94362 (1976), have reported several 2-oxoimidazo[4,5-c]quinolines, and Berenyi et al., *J. Heterocyclic Chem.* 18, 1537–1540 (1981), have reported certain 2-oxoimidazo[4,5-c]quinolines.

Certain 1H-imidazo[4,5-c]quinolin-4-amines and 1- and 2-substituted derivatives thereof were later found to be useful as antiviral agents, bronchodilators and immunomodulators. These are described in, inter alia, U.S. Pat. Nos. 4,689,338; 4,698,348; 4,929,624; 5,037,986; 5,268,376; 5,346,905; and 5,389,640, all of which are incorporated herein by reference.

There continues to be interest in the imidazoquinoline ring system.

Certain 1H-imidazo[4,5-c]naphthyridine-4-amines, 1H-imidazo [4,5-c]pyridin-4-amines, and 1H-imidazo[4,5-c]quinolin-4-amines having an ether containing substituent at the 1 position are known. These are described in U.S. Pat. Nos. 5,268,376; 5,389,640; 5,494,916; and WO 99/29693.

Despite these attempts to identify compounds that are useful as immune response modifiers, there is a continuing need for compounds that have the ability to modulate the immune response, by induction of cytokine biosynthesis or other mechanisms.

SUMMARY OF THE INVENTION

We have found a new class of compounds that are useful in inducing cytokine biosynthesis in animals. Accordingly, this invention provides imidazoquinoline-4-amine and tetrahydroimidazoquinoline-4-amine compounds that have a thioether containing substituent at the 1-position. The compounds are defined by Formulas (I) and (II), which are defined in more detail infra. These compounds share the general structural formula:

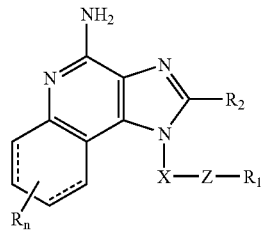

wherein X, Z, $R_1$, $R_2$, and R are as defined herein for each class of compounds having formulas (I) and (II).

The compounds of formulas (I) and (II) are useful as immune response modifiers due to their ability to induce cytokine biosynthesis and otherwise modulate the immune response when administered to animals. This makes the compounds useful in the treatment of a variety of conditions such as viral diseases and tumors that are responsive to such changes in the immune response.

The invention further provides pharmaceutical compositions containing the immune response modifying compounds, and methods of inducing cytokine biosynthesis in an animal, treating a viral infection in an animal, and/or treating a neoplastic disease in an animal by administering a compound of Formula (I) or (II) to the animal.

In addition, the invention provides methods of synthesizing the compounds of the invention.

DETAILED DESCRIPTION OF THE INVENTION

As mentioned earlier, we have found certain compounds that induce cytokine biosynthesis and modify the immune response in animals. Such compounds are represented by Formulas (I) and (II) as shown below.

Imidazoquinoline compounds of the invention, which have thioether functionality at the 1-position are represented by Formula (I):

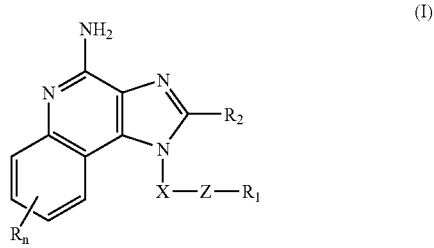

wherein: X is —$CHR_3$—, —$CHR_3$-alkyl-, or —$CHR_3$-alkenyl-;

Z is —S—, —SO—, or —$SO_2$—;

$R_1$ is selected from the group consisting of:
 -alkyl;
 -aryl;
 -heteroaryl;
 -heterocyclyl;
 -alkenyl;
 —$R_4$-aryl;

—$R_4$-heteroaryl;
—$R_4$-heterocyclyl;
$R_2$ is selected from the group consisting of:
-hydrogen;
-alkyl;
-alkenyl;
-aryl;
-heteroaryl;
-heterocyclyl;
-alkyl-Y-alkyl;
-alkyl-Y-alkenyl;
-alkyl-Y-aryl; and
-alkyl or alkenyl substituted by one or more substituents selected from the group consisting of:
—OH;
-halogen;
—$N(R_3)_2$;
—CO—$N(R_3)_2$;
—CO—$C_{1-10}$ alkyl;
—CO—O—$C_{1-10}$ alkyl;
—$N_3$;
-aryl;
-heteroaryl;
-heterocyclyl;
—CO-aryl; and
—CO-heteroaryl;
each $R_3$ is independently H or $C_{1-10}$ alkyl;
each $R_4$ is independently alkyl or alkenyl;
each Y is independently or —O— or —$S(O)_{0-2}$—;
n is 0 to 4; and
each R present is independently selected from the group consisting of $C_{1-10}$ alkyl, $C_{1-10}$ alkoxy, hydroxy, halogen and trifluoromethyl;

or a pharmaceutically acceptable salt thereof.

The invention also includes tetrahydroimidazoquinoline compounds that bear a thioether containing substituent at the 1-position. Such tetrahydroimidazoquinoline compounds are represented by Formula (II):

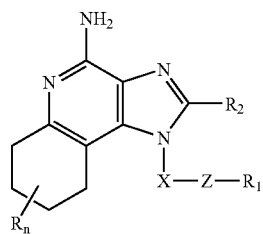

wherein: X is —$CHR_3$—, —$CHR_3$-alkyl-, or —$CHR_3$-alkenyl-;
Z is —S—, —SO—, or —$SO_2$—;
$R_1$ is selected from the group consisting of:
-alkyl;
-aryl;
-heteroaryl;
-heterocyclyl;
-alkenyl;
—$R_4$-aryl;
—$R_4$-heteroaryl; and
—$R_4$-heterocyclyl;
$R_2$ is selected from the group consisting of:
-hydrogen;
-alkyl;
-alkenyl;
-aryl;
-heteroaryl;
-heterocyclyl;
-alkyl-Y-alkyl;
-alkyl-Y-alkenyl;
-alkyl-Y-aryl; and
-alkyl or alkenyl substituted by one or more substituents selected from the group consisting of:
—OH;
-halogen;
—$N(R_3)_2$;
—CO—$N(R_3)_2$;
—CO—$C_{1-10}$alkyl;
—CO—O—$C_{1-10}$alkyl;
—$N_3$;
-aryl;
-heteroaryl;
-heterocyclyl;
—CO-aryl; and
—CO-heteroaryl;
each $R_3$ is independently H or $C_{1-10}$ alkyl;
each $R_4$ is independently alkyl or alkenyl;
each Y is independently —O— or —$S(O)_{0-2}$—;
n is 0 to 4; and
each R present is independently selected from the group consisting of $C_{1-10}$ alkyl, $C_{1-10}$ alkoxy, hydroxy, halogen and trifluoromethyl;

or a pharmaceutically acceptable salt thereof.

Preparation of the Compounds

Compounds of the invention can be prepared according to Reaction Scheme I where R, $R_1$, $R_2$, X and n are as defined above.

In step (1) of Reaction Scheme I a 4-chloro-3-nitroquinoline of Formula X is reacted with an amine of formula HO—X—$NH_2$ to provide a 3-nitroquinolin-4-amine of Formula XI. The reaction can be carried out by adding the amine to a solution of a compound of Formula X in a suitable solvent such as chloroform or dichloromethane in the presence of triethylamine and optionally heating. Many quinolines of Formula X are known compounds (see for example, U.S. Pat. No. 4,689,338 and references cited therein). Many amines of formula HO—X—$NH_2$ are commercially available; others can be readily prepared using known synthetic routes.

In step (2) of Reaction Scheme I a 3-nitroquinolin-4-amine of Formula XI is chlorinated to provide a 3-nitroquinolin-4-amine of Formula XII. Conventional chlorinating agents can be used. Preferably the reaction is carried out by combining a compound of Formula XI with thionyl chloride in a suitable solvent such as dichloromethane and heating. Alternatively the reaction may be run neat.

In step (3) of Reaction Scheme I a 3-nitroquinolin-4-amine of Formula XII is reduced to provide a quinoline-3,4-diamine of Formula XIII. Preferably, the reduction is carried out using a conventional heterogeneous hydrogenation catalyst such as platinum on carbon. The reaction can conveniently be carried out on a Parr apparatus in a suitable solvent such as toluene.

In step (4) of Reaction Scheme I a quinoline-3,4-diamine of Formula XIII is reacted with a carboxylic acid or an equivalent thereof to provide a 1H-imidazo[4,5-c]quinoline of Formula XIV. Suitable equivalents to a carboxylic acid include orthoesters, and 1,1-dialkoxyalkyl alkanoates. The carboxylic acid or equivalent is selected such that it will provide the desired $R_2$ substituent in a compound of Formula XIV. For example, triethyl orthoformate will provide a compound where $R_2$ is hydrogen and trimethyl orthovalerate will provide a compound where $R_2$ is butyl. The reaction can be run in the absence of solvent or in an inert solvent such as toluene. The reaction is run with sufficient heating to drive off any alcohol or water formed as a byproduct of the reaction. Optionally a catalyst such as pyridine hydrochloride can be included.

Alternatively, step (4) can be carried out by (i) reacting the diamine of Formula XIII with an acyl halide of Formula $R_2C(O)Cl$ or $R_2C(O)Br$ and then (ii) cyclizing. In part (i) the acyl halide is added to a solution of the diamine in a suitable solvent such as pyridine. The reaction can be carried out at ambient temperature. In part (ii) the product of part (i) is heated in pyridine in the presence of pyridine hydrochloride.

In step (5) of Reaction Scheme I a 1H-imidazo[4,5-c] quinoline of Formula XIV is oxidized to provide a 1H-imidazo[4,5-c]quinoline-5N-oxide of Formula XV using a conventional oxidizing agent capable of forming N-oxides. Preferably a solution of a compound of Formula XIV in a suitable solvent such as chloroform or dichloromethane is treated with 3-chloroperoxybenzoic acid at ambient temperature.

In step (6) of Reaction Scheme I a 1H-imidazo[4,5-c] quinoline-5N-oxide of Formula XV is aminated to provide a 1H-imidazo[4,5-c]quinolin-4-amine of Formula XVI. Step (6) involves (i) reacting a compound of Formula XV with an acylating agent and then (ii) reacting the product with an aminating agent. Part (i) of step (6) involves reacting an N-oxide of Formula XV with an acylating agent. Suitable acylating agents include alkyl- or arylsulfonyl chlorides (e.g., benezenesulfonyl chloride, methanesulfonyl chloride, p-toluenesulfonyl chloride). Arylsulfonyl chlorides are preferred. Para-toluenesulfonyl chloride is most preferred. Part (ii) of step (6) involves reacting the product of part (i) with an excess of an aminating agent. Suitable aminating agents include ammonia (e.g., in the form of ammonium hydroxide) and ammonium salts (e.g., ammonium carbonate, ammonium bicarbonate, ammonium phosphate). Ammonium hydroxide is preferred. The reaction is preferably carried out by dissolving the N-oxide of Formula XV in an inert solvent such as dichloromethane or chloroform, adding the aminating agent to the solution, and then slowly adding the acylating agent.

In step (7) of Reaction Scheme I a 1H-imidazo[4,5-c] quinolin-4-amine of Formula XVI is reacted with a compound of Formula $R_1$—SNa to provide a 1H-imidazo[4,5-c]quinolin-4-amine of Formula XVII which is a subgenus of Formula I. The reaction can be carried out by combining a compound of Formula XVI with a compound of formula $R_1SNa$ in a suitable solvent such as N,N-dimethylformamide or dimethyl sulfoxide and heating (60–80° C.). The product or a pharmaceutically acceptable salt thereof can be isolated using conventional methods.

In step (8) of Reaction Scheme I a 1H-imidazo[4,5-c] quinolin-4-amine of Formula XVII is oxidized using a conventional oxidizing agent to provide a 1H-imidazo[4,5-c]quinolin-4-amine of Formula XVIII which is a subgenus of Formula I. Preferably a solution of a compound of Formula XVII in a suitable solvent such as chloroform or dichloromethane is treated with 3-chloroperoxybenzoic acid at ambient temperature. The degree of oxidation is controlled by adjusting the amount of 3-chloroperoxybenzoic acid used in the reaction; i.e., using approximately one equivalent will provide the sulfoxide whereas using two equivalents will provide the sulfone. The product or a pharmaceutically acceptable salt thereof can be isolated using conventional methods.

Reaction Scheme I

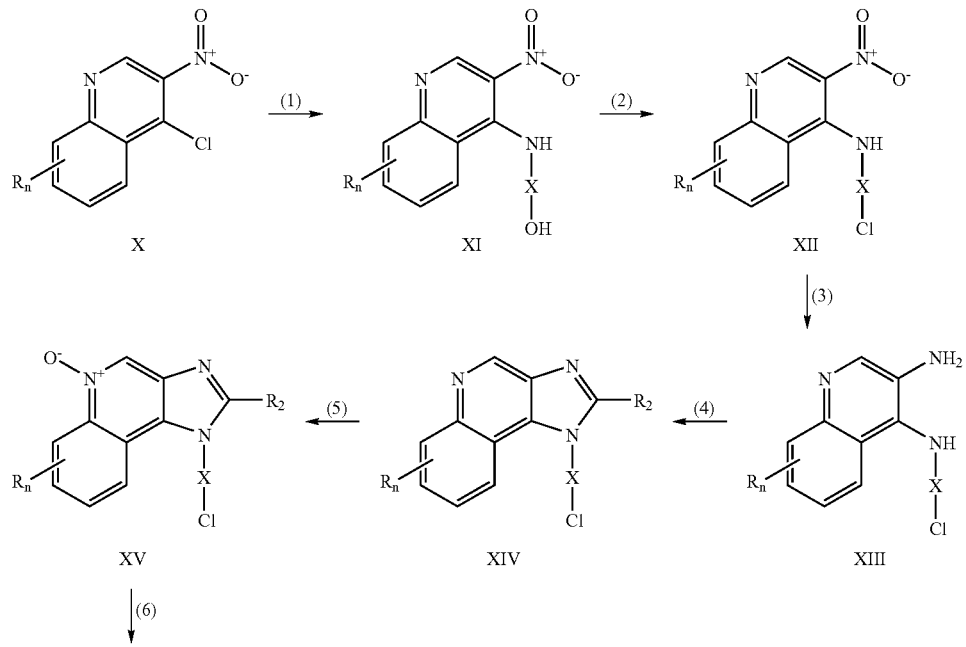

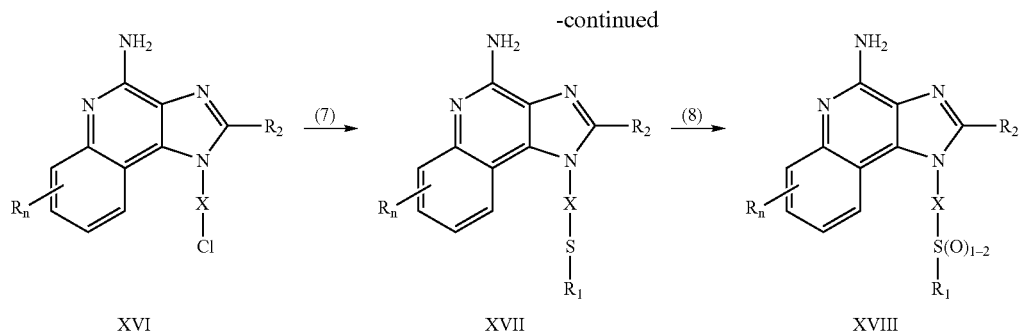

Compounds of the invention can be prepared according to Reaction Scheme II where R, $R_1$, $R_2$, X and n are as defined above.

In step (1) of Reaction Scheme II a 3-nitroquinolin-4-amine of Formula XII is reacted with a compound of the Formula $R_1$—SNa using the method of step (7) of Reaction Scheme I to provide a 3-nitroquinolin-4-amine of Formula XIX.

In step (2) of Reaction Scheme II a 3-nitroquinolin-4-amine of Formula XIX is reduced using the method of step (3) of Reaction Scheme I to provide a quinoline-3,4-diamine of Formula XX.

In step (3) of Reaction Scheme II a quinoline-3,4-diamine of Formula XX is cyclized using the method of step (4) of Reaction Scheme I to provide a 1H-imidazo[4,5-c]quinoline of Formula XXI.

In step (4) of Reaction Scheme II a 1H-imidazo[4,5-c]quinoline of Formula XXI is oxidized to provide a 1H-imidazo[4,5-c]quinolin-5N-oxide of Formula XXII using a conventional oxidizing agent. Preferably a solution of a compound of Formula XXI in a suitable solvent such as chloroform or dichloromethane is treated with at least three equivalents of 3-chloroperoxybenzoic acid at ambient temperature.

In step (5) of Reaction Scheme II a 1H-imidazo[4,5-c]quinolin-5N-oxide of Formula XXII is aminated using the method of step (6) of Reaction Scheme I to provide a 1H-imidazo[4,5-c]quinolin-4-amine of Formula XVIII which is a subgenus of Formula I. The product or a pharmaceutically acceptable salt thereof can be isolated using conventional methods.

Reaction Scheme II

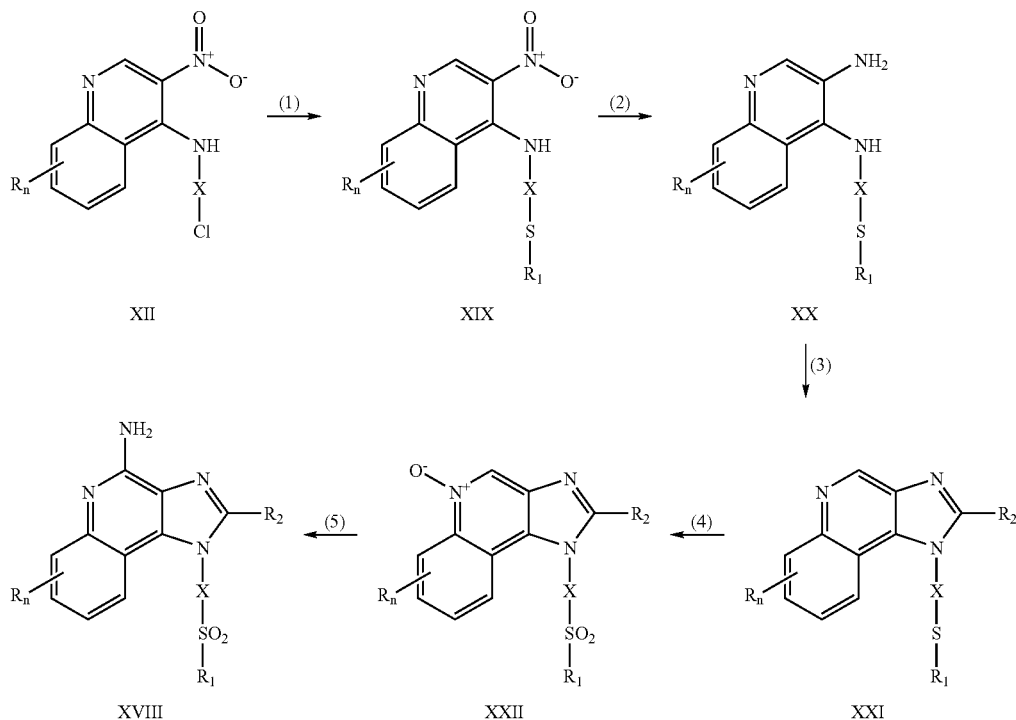

Compounds of the invention can be prepared according to Reaction Scheme III where R, $R_1$, $R_2$, X and n are as defined above.

In step (1) of Reaction Scheme III a 3-nitro-4-amino-quinolin-1-yl alcohol of Formula XI is protected with a tert-butyldimethylsilyl group using conventional methods. Preferably a compound of Formula XI is combined with tert-butyldimethylsilyl chloride in a suitable solvent such as chloroform in the presence of triethylamine and a catalytic amount of 4-dimethylaminopyridine.

In step (2) of Reaction Scheme III a protected 3-nitro-4-amino-quinolin-1-yl alcohol of Formula XIII is reduced using the method of step (3) of Reaction Scheme I to provide a protected 3,4-diamino-quinolin-1-yl alcohol of Formula XXIV.

In step (3) of Reaction Scheme III a protected 3,4-diamino-quinolin-1-yl alcohol of Formula XXIV is cyclized using the method of step (4) of Reaction Scheme I to provide a 1H-imidazo[4,5-c]quinoline of Formula XXV.

In step (4) of Reaction Scheme III a 1H-imidazo[4,5-c]quinoline of Formula XXV is oxidized using the method of step (5) of Reaction Scheme I to provide a 1H-imidazo[4,5-c]quinolin-5N-oxide of Formula XXVI.

In step (5) of Reaction Scheme III a 1H-imidazo[4,5-c]quinolin-5N-oxide of Formula XXVI is aminated using the method of step (6) of Reaction Scheme I to provide a 1H-imidazo[4,5-c]quinolin-4-amine of Formula XXVII.

In step (6) of Reaction Scheme III the protecting group is removed from a 1H-imidazo[4,5-c]quinolin-4-amine of Formula XXVII to provide a 1H-imidazo[4,5-c]quinolin-4-amine of Formula XXVIII. Preferably a solution of a compound of Formula XXVII in a suitable solvent such as tetrahydrofuran is treated with tetrabutylammonium fluoride. Some compounds of Formula XXVIII are known, see for example, Gerster, U.S. Pat. No. 4,689,338 and Gerster et al., U.S. Pat. No. 5,605,899.

In step (7) of Reaction Scheme III a 1H-imidazo[4,5-c]quinolin-4-amine of Formula XXVIII is chlorinated using conventional methods to provide a 1H-imidazo[4,5-c]quinolin-4-amine of Formula XVI. A compound of Formula XXVIII can be heated neat with thionyl chloride. Alternatively, phosphorous oxychloride can be added in a controlled fashion to a solution of a compound of Formula XXVIII in a suitable solvent such as N,N-dimethylformamide in the presence of triethylamine.

Steps (8) and (9) of Reaction Scheme III can be carried out in the same manner as steps (7) and (8) respectively of Reaction Scheme I.

Reaction Scheme III

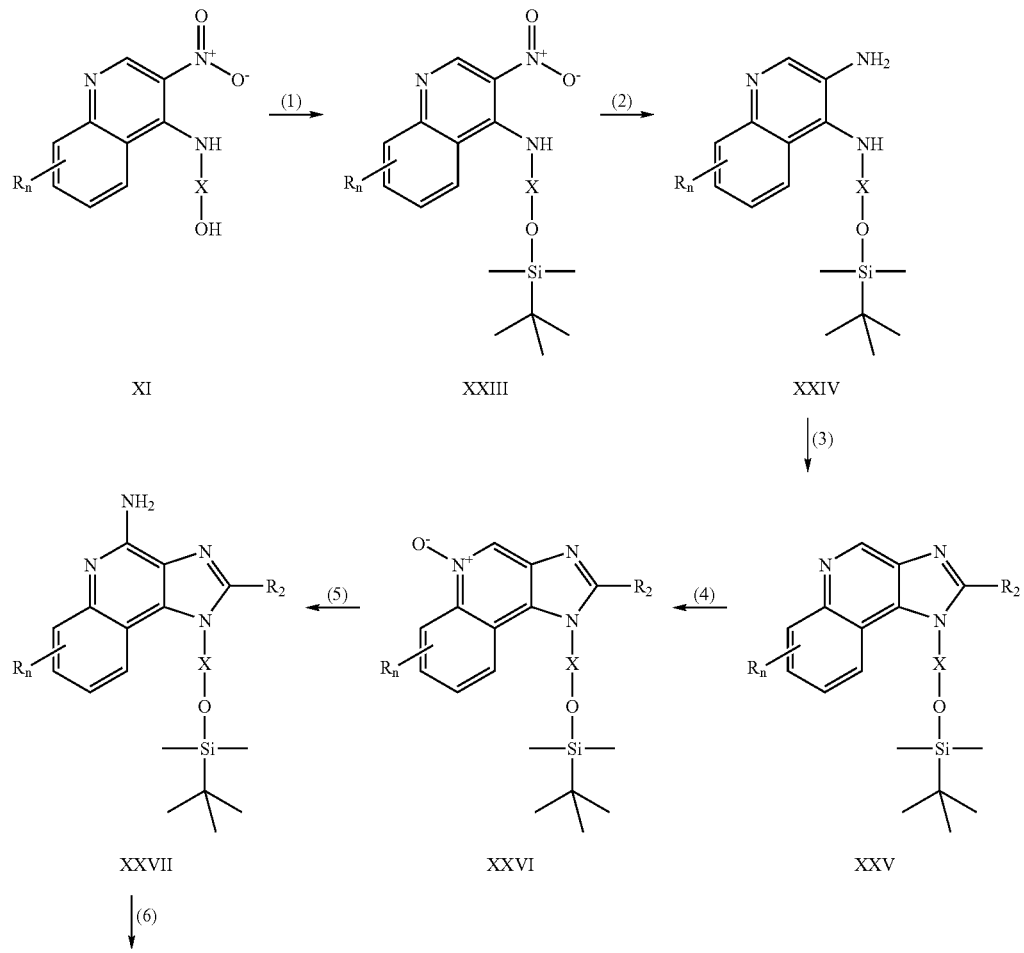

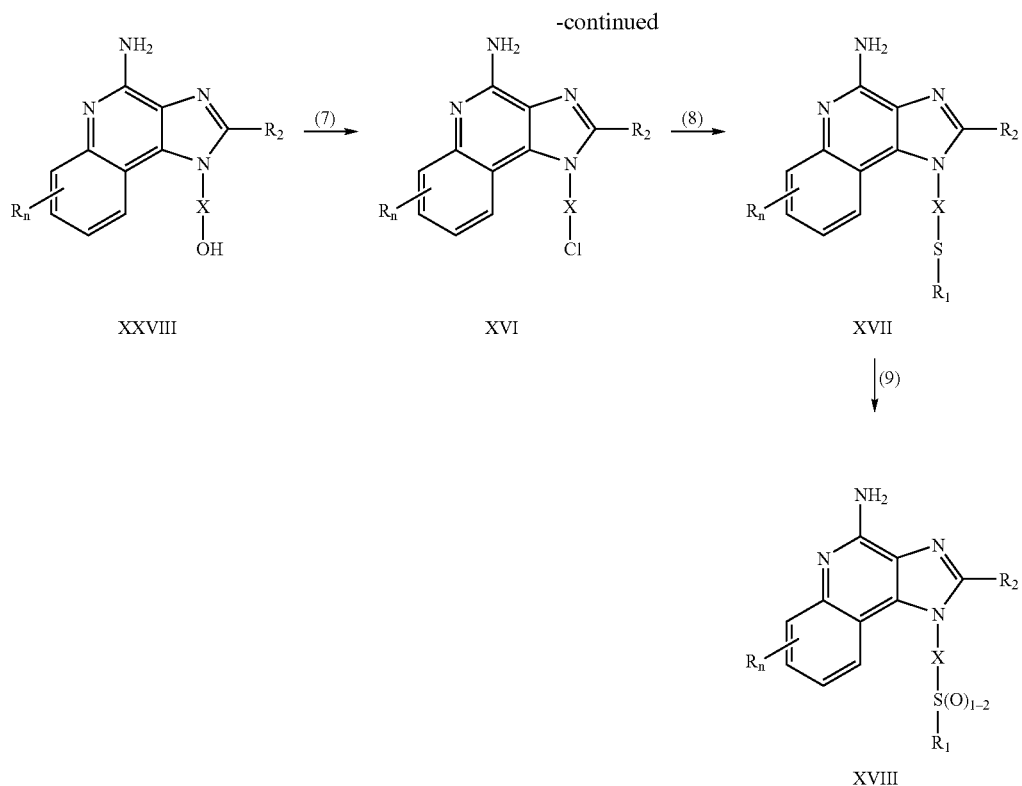

Compounds of the invention can be prepared according to Reaction Scheme IV where R, $R_1$, $R_2$, X and n are as defined above and BOC is tert-butoxycarbonyl.

In step (1) of Reaction Scheme IV the hydroxy group of a 6,7,8,9-tetrahydro-1H-imidazo[4,5-c]quinolin-1-yl alcohol of Formula XXIX is protected with a tert-butyldimethylsilyl group using the method of step (1) of Reaction Scheme III. Compounds of Formula XXIX are known or can be prepared using known synthetic methods, see for example, Nikolaides, et al., U.S. Pat. No. 5,352,784 and Lindstrom, U.S. Pat. No. 5,693,811 and references cited therein.

In step (2) of Reaction Scheme IV the amino group of a 1H-imidazo[4,5-c]quinolin-4-amine of Formula XXX is protected using conventional methods to provide a protected 1H-imidazo[4,5-c]quinoline of Formula XXXI. Preferably a compound of Formula XXX is treated with di-tert-butyl dicarbonate in a suitable solvent such as tetrahydrofuran in the presence of triethylamine and 4-dimethylaminopyridine. The reaction cap be run at an elevated temperature (60° C.).

In step (3) of Reaction Scheme IV the tert-butyldimethylsilyl protecting group of a compound of Formula XXXI is removed using the method of step (6) of Reaction Scheme III to provide a 1H-imidazo[4,5-c]quinolin-1yl alcohol of Formula XXXII.

In step (4) of Reaction Scheme IV a 1H-imidazo[4,5-c]quinolin-1yl alcohol of Formula XXXII is converted to a methanesulfonate of Formula XXXIII. Preferably a solution of a compound of Formula XXXII in a suitable solvent such as dichloromethane is treated with methanesulfonyl chloride in the presence of triethylamine. The reaction can be run at a reduced temperature (–10° C.).

In step (5) of Reaction Scheme IV a methanesulfonate of Formula XXXIII is reacted with a thiol of formula $R_1SH$ to provide a thioether of Formula XXXIV. Preferably a solution of a compound of Formula XXXIII in a suitable solvent such as N,N-dimethylformamide is treated with the thiol in the presence of triethylamine. The reaction can be run at an elevated temperature (80° C.).

In step (6) of Reaction Scheme IV the tert-butoxycarbonyl protecting groups are removed by hydrolysis under acidic conditions to provide a 1H-imidazo[4,5]quinolin-4-amine of Formula XXXV which is a subgenus of Formula II. Preferably a solution of a compound of Formula XXXIV in a suitable solvent such as dichloromethane is treated at ambient temperature with a solution of hydrochloric acid in dioxane. The product or a pharmaceutically acceptable salt thereof can be isolated using conventional methods.

In step (7) of Reaction Scheme IV a thioether of Formula XXXV is oxidized using the method of step (8) of Reaction Scheme I to provide a sulfone or sulfoxide of Formula XXXVI which is a subgenus of Formula II. The product or a pharmaceutically acceptable salt thereof can be isolated using conventional methods.

Reaction Scheme IV

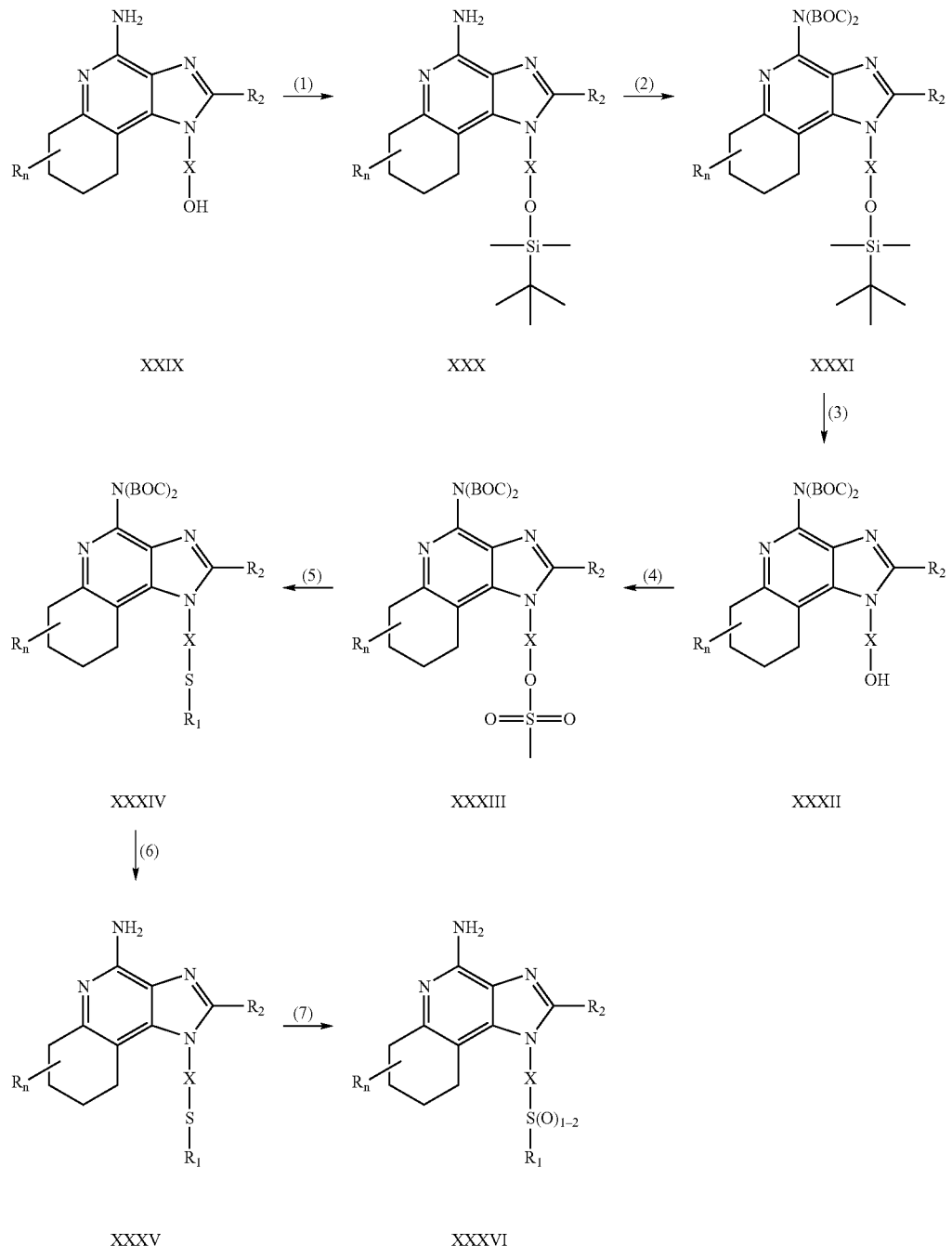

Compounds of the invention can be prepared according to Reaction Scheme V where R, $R_1$, $R_2$, X and n are as defined above.

In step (1) of Reaction Scheme V a 6,7,8,9-tetrahydro-1H-imidazo[4,5-c]quinolin-1-yl alcohol of Formula XXIX is chlorinated using the method of step (7) of Reaction Scheme III to provide a compound of Formula XXXVII.

In step (2) of Reaction Scheme V a compound of Formula XXXVII is reacted with a compound of formula $R_1$—SNa using the method of step (7) of Reaction Scheme I to provide a thioether of Formula XXXV which is a subgenus of Formula II. The product or a pharmaceutically acceptable salt thereof can be isolated using conventional methods.

In step (3) of Reaction Scheme V a thioether of Formula XXXV is oxidized using the method of step (8) of Reaction Scheme I to provide a sulfone or sulfoxide of Formula XXXVI which is a subgenus of Formula II. The product or a pharmaceutically acceptable salt thereof can be isolated using conventional methods.

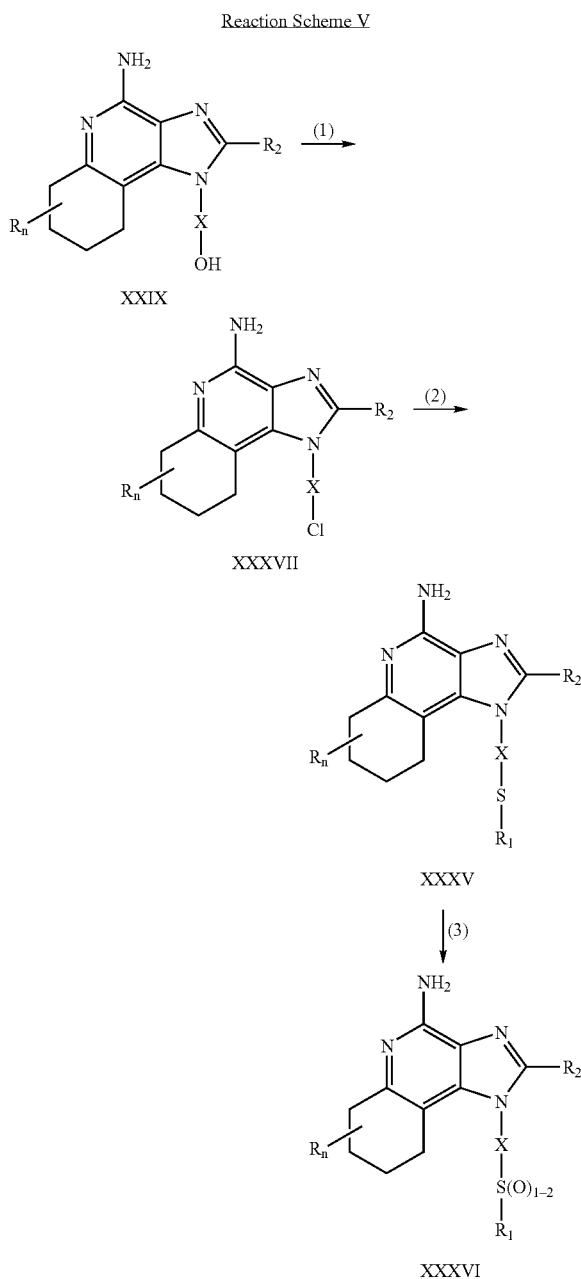

Reaction Scheme V

As used herein, the terms "alkyl", "alkenyl" and the prefix "alk-" are inclusive of both straight chain and branched chain groups and of cyclic groups, i.e. cycloalkyl and cycloalkenyl. Unless otherwise specified, these groups contain from 1 to 20 carbon, atoms, with alkenyl groups containing from 2 to 20 carbon atoms. Preferred groups have a total of up to 10 carbon atoms. Cyclic groups can be monocyclic or polycyclic and preferably have from 3 to 10 ring carbon atoms. Exemplary cyclic groups include cyclopropyl, cyclopropylmethyl, cyclopentyl, cyclohexyl and adamantyl.

In addition, the alkyl and alkenyl portions of —X— groups can be unsubstituted or substituted by one or more substituents, which substituents are selected from the groups consisting of alkyl, alkenyl, aryl, heteroaryl, heterocyclyl, arylalkyl, heteroarylalkyl, and heterocyclylalkyl.

The term "haloalkyl" is inclusive of groups that are substituted by one or more halogen atoms, including perfluorinated groups. This is also true of groups that include the prefix "halo-", Examples of suitable haloalkyl groups are chloromethyl, trifluoromethyl, and the like.

The term "aryl" as used herein includes carbocyclic aromatic rings or ring systems. Examples of aryl groups include phenyl, naphthyl, biphenyl, fluorenyl and indenyl. The term "heteroaryl" includes aromatic rings or ring systems that contain at least one ring hetero atom (e.g., O, S, N). Suitable heteroaryl groups include furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl benzimidazolyl, quinoxalinyl, benzothiazolyl, naphthyridinyl, isoxazolyl, isothiazolyl, purinyl, quinazolinyl, and so on.

"Heterocyclyl" includes non-aromatic rings or ring systems that contain at least one ring hetero atom (e.g., O, S, N) and includes all of the fully-saturated and partially unsaturated derivatives of the above mentioned heteroaryl groups. Exemplary heterocyclic groups include pyrrolidinyl, tetrahydrofuranyl, morpholinyl, thiomorpholinyl, piperidinyl, piperazinyl, thiazolidinyl, imidazolidinyl, isothiazolidinyl, and the like.

The aryl, heteroaryl, and heterocyclyl groups can be unsubstituted or substituted by one or more substituents independently selected from the group consisting of alkyl, alkoxy, alkylthio, haloalkyl, haloalkoxy, haloalkylthio, halogen, nitro, hydroxy, mercapto, cyano, carboxy, formyl, aryl, aryloxy, arylthio, arylalkoxy, arylalkylthio, heteroaryl, heteroaryloxy, heteroarylthio, heteroarylalkoxy, heteroarylalkylthio, amino, alkylamino, dialkylamino, heterocyclyl, heterocycloalkyl, alkylcarbonyl, alkenylcarbonyl, alkoxycarbonyl, haloalkylcarbonyl, haloalkoxycarbonyl, alkylthiocarbonyl, arylcarbonyl, heteroarylcarbonyl, aryloxycarbonyl, heteroaryloxycarbonyl, arylthiocarbonyl, heteroarylthiocarbonyl, alkanoyloxy, alkanoylthio, alkanoylamino, arylcarbonyloxy, arylcarbonylthio, alkylaminosulfonyl, alkylsulfonyl, arylsulfonyl, heteroarylsulfonyl, aryldiazinyl, alkylsulfonylamino, arylsulfonylamino, arylalkylsulfonylamino, alkylcarbonylamino, alkenylcarbonylamino, arylcarbonylamino, arylalkylcarbonylamino, heteroarylcarbonylamino, heteroarylalkycarbonylamino, alkylsulfonylamino, alkenylsulfonylamino, arylsulfonylamino, arylalkylsulfonylamino, heteroarylsulfonylamino, heteroarylalkylsulfonylamino, alkylaminocarbonylamino, alkenylaminocarbonylamino, arylaminocarbonylamino, arylalkylaminocarbonylamino, heteroarylaminocarbonylamino, heteroarylalkylcarbonylamino, and, in the case of heterocyclyl, oxo. If any other groups are identified as being "substituted" or "optionally substituted", then those groups can also be substituted by one or more of the above enumerated substituents.

Certain substituents are generally preferred. For example, preferred X groups include ethylene and n-butylene and preferred $R_1$ groups are alkyl and aryl, with phenyl or substituted phenyl a preferred aryl group. Preferably no R substituents are present (i.e., n is 0). Preferred $R_2$ groups include hydrogen, alkyl groups having 1 to 4 carbon atoms (i.e., methyl, ethyl, propyl, isopropyl, n-butyl, sec-butyl, isobutyl, and cyclopropylmethyl), methoxyethyl, and ethoxymethyl. One or more of these preferred substituents, if present, can be present in the compounds of the invention in any combination.

The invention is inclusive of the compounds described herein in any of their pharmaceutically acceptable forms, including isomers (e.g., diastereomers and enantiomers), salts, solvates, polymorphs, and the like. In particular, if a compound is optically active, the invention specifically includes each of the compound's enantiomers as well as racemic mixtures of the enantiomers.

Pharmaceutical Compositions and Biological Activity

Pharmaceutical compositions of the invention contain a therapeutically effective amount of a compound of the invention as described above in combination with a pharmaceutically acceptable carrier.

The term "a therapeutically effective amount" means an amount of the compound sufficient to induce a therapeutic effect, such as cytokine induction, antitumor activity, and/or antiviral activity. Although the exact amount of active compound used in a pharmaceutical composition of the invention will vary according to factors known to those of skill in the art, such as the physical and chemical, nature of the compound, the nature of the carrier, and the intended dosing regimen, it is anticipated that the compositions of the invention will contain sufficient active ingredient to provide a dose of about 100 ng/kg to about 50 mg/kg, preferably about 10 µg/kg to about 5 mg/kg, of the compound to the subject. Any of the conventional dosage forms may be used, such as tablets, lozenges, parenteral formulations, syrups, creams, ointments, aerosol formulations, transdermal patches, transmucosal patches and the like.

The compounds of the invention can be administered as the single therapeutic agent in the treatment regimen, or the compounds of the invention may be administered in combination with one another or with other active agents, including additional immune response modifiers, antivirals, antibiotics, etc.

The compounds of the invention have been shown to induce the production of certain cytokines in experiments performed according to the tests set forth below. These results indicate that the compounds are useful as immune response modifiers that can modulate the immune response in a number of different ways, rendering them useful in the treatment of a variety of disorders.

Cytokines whose production may be induced by the administration of compounds according to the invention generally include interferon-α (IFN-α) and/or tumor necrosis factor-α (TNF-α) as well as certain interleukins (IL). Cytokines whose biosynthesis may be induced by compounds of the invention include IFN-α, TNF-α, IL-1, IL-6, IL-10 and IL-12, and a variety of other cytokines. Among other effects, these and other cytokines can inhibit virus production and tumor cell growth, making the compounds useful in the treatment of viral diseases and tumors. Accordingly, the invention provides a method of inducing cytokine biosynthesis in an animal comprising administering an effective amount of a compound or composition of the invention to the animal.

Certain compounds of the invention have been found to preferentially induce the expression of IFN-α in a population of hematopoietic cells such as PBMCs (peripheral blood mononuclear cells) containing pDC2 cells (precursor dendritic cell-type 2) without concomitant production of significant levels of inflammatory cytokines.

In addition to the ability to induce the production of cytokines, the compounds of the invention affect other aspects of the innate immune response. For example, natural killer cell activity may be stimulated, an effect that may be due to cytokine induction. The compounds may also activate macrophages, which in turn stimulates secretion of nitric oxide and the production of additional cytokines. Further, the compounds may cause proliferation and differentiation of B-lymphocytes.

Compounds of the invention also have an effect on the acquired immune response. For example, although there is not believed to be any direct effect on T cells or direct induction of T cell cytokines, the production of the T helper type 1 (Th1) cytokine IFN-γ is induced indirectly and the production of the T helper type 2 (Th2) cytokines IL-4, IL-5 and IL-13 are inhibited upon administration of the compounds. This activity means that the compounds are useful in the treatment of diseases where upregulation of the Th1 response and/or downregulation of the Th2 response is desired. In view of the ability of compounds of the invention to inhibit the Th2 immune response, the compounds are expected to be useful in the treatment of atopic diseases, e.g., atopic dermatitis, asthma, allergy, allergic rhinitis; systemic lupus erythematosis; as a vaccine adjuvant for cell mediated immunity; and possibly as a treatment for recurrent fungal diseases and chlamydia.

The immune response modifying effects of the compounds make them useful in the treatment of a wide variety of conditions. Because of their ability to induce the production of cytokines such as IFN-α and/or TNF-α, the compounds are particularly useful in the treatment of viral diseases and tumors. This immunomodulating activity suggests that compounds of the invention are useful in treating diseases such is, but not limited to, viral diseases including genital warts; common warts; plantar warts; Hepatitis B; Hepatitis C; Herpes Simplex Virus Type I and Type II; molluscum contagiosum; variola, particularly variola major; HIV; CMV; VZV; rhinovirus; adenovirus; influenza; and para-influenza; intraepithelial neoplasias such as cervical intraepithelial neoplasia; human papillomavirus (HPV) and associated neoplasias; fungal diseases, e.g. candida, aspergillus, and cryptococcal meningitis; neoplastic diseases, e.g., basal cell carcinoma, hairy cell leukemia, Kaposi's sarcoma, renal cell carcinoma, squamous cell carcinoma, myelogenous leukemia, multiple myeloma melanoma, non-Hodgkin's lymphoma, cutaneous T-cell lymphoma, and other cancers; parasitic diseases, e.g. pneumocystis carnii, cryptosporidiosis, histoplasmosis, toxoplasmosis, trypanosome infection, and leishmaniasis; and bacterial infections, e.g., tuberculosis, and mycobacterium avium. Additional diseases or conditions that can be treated using the compounds of the invention include actinic keratosis; eczema; eosinophilia; essential thrombocythaemia; leprosy; multiple sclerosis; Ommen's syndrome; discoid lupus; Bowen's disease; Bowenoid papulosis; alopecia areata; the inhibition of Keloid formation after surgery and other types of post-surgical scars. In addition, these compounds could enhance or stimulate the healing of wounds, including chronic wounds. The compounds may be useful for treating the opportunistic infections and tumors that occur after suppression of cell mediated immunity in, for example, transplant patients, cancer patients and HIV patients.

An amount of a compound effective to induce cytokine biosynthesis is an amount sufficient to cause one or more cell types, such as monocytes, macrophages, dendritic cells and B-cells to produce an amount of one or more cytokines such as, for example, IFN-α, TNF-α, IL-1, IL-6, IL-10 and IL-12 that is increased over the background level of such cytokines. The precise amount will vary according to factors known in the art but is expected to be a dose of about 100 ng/kg to about 50 mg/kg, preferably about 10 µg/kg to about 5 mg/kg. The invention also provides a method of treating a viral infection in an animal and a method of treating a neoplastic disease in an animal comprising administering an effective amount of a compound or composition of the invention to the animal. An amount effective to treat or inhibit a viral infection is an amount that will cause a reduction in one or more of the manifestations of viral infection, such as viral lesions, viral load, rate of virus production, and mortality as compared to untreated control animals. The precise amount will vary according to factors known in the art but is expected to be a dose of about 100 ng/kg to about 50 mg/kg, preferably about 10 μg/kg to about 5 mg/kg. An amount of a compound effective to treat a neoplastic condition is an amount that will cause a reduction in tumor size or in the number of tumor foci. Again, the precise amount will vary according to factors known in the art but is expected to be a dose of about 100 ng/kg to about 50 mg/kg, preferably about 10 μg/kg to about 5 mg/kg.

The invention is further described by the following examples, which are provided for illustration only and are not intended to be limiting in any way.

EXAMPLE 1

2-butyl-1-[4-(phenylthio)butyl]-1H-imidazo[4,5-c]quinolin-4-amine

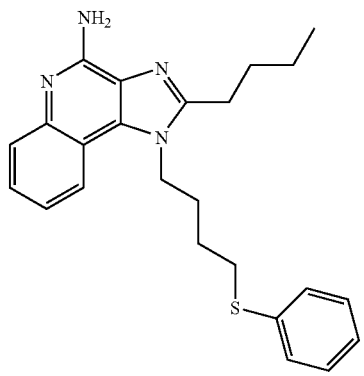

Part A

A round bottom flask was charged with a magnetic stir bar, 4-chloro-3-nitroquinoline (109.70 g, 525.87 mmol) and dichloromethane (500 mL). To the solution was added triethylamine (79.82 g, 788.81 mmol) and 4-amino-1-butanol (46.87 g, 525.87 mmol) to give a homogeneous, dark yellow solution. The reaction was judged to be complete after heating at reflux for 30 minutes. The solution was cooled and then partitioned between chloroform and saturated aqueous ammonium chloride. The layers were separated and the aqueous layer was extracted with chloroform (1×). The organic layers were combined and then concentrated under reduced pressure to afford of 4-[(3-nitroquinolin)amino]butan-1-ol (104.67 g, 400.60 mmol) as a dark yellow solid. This material was used without further purification.

Part B

A round bottom flask was charged with a magnetic stir bar, 4-[(3-nitroquinolin-4-yl)amino]butan-1-ol (5.0 g, 19.14 mmol), triethylamine (2.91 g, 28.71 mmol), tert-butyldimethylsilyl chloride (3.75 g, 24.9 mmol), 4-dimethylaminopyridine (0.10 g) and chloroform (40 mL) to give a dark yellow solution. The reaction was judged was to complete after stirring at ambient temperature for 2 hours. The solution was partitioned between ethyl acetate and saturated aqueous ammonium chloride. The layers were separated and the organic layer was washed with saturated aqueous sodium bicarbonate, dried over anhydrous sodium sulfate, filtered and then concentrated under reduced pressure to afford N-(4-{[tert-butyl(dimethyl)silyl]oxy}butyl)-3-nitroquinolin-4-amine (6.05 g, 16.11 mmol) as a yellow-green solid. This material was used without further purification. MS (CI) for $C_{19}H_{29}N_3O_3Si$ m/z 376 (MH+), 342, 210.

Part C

A Parr vessel was charged with N-(4-{[tert-butyl(dimethyl)silyl]oxy}butyl)-3-nitroquinolin-4-amine (6.05 g, 16.11 mmol), 5% platinum on carbon (3.0 g), and toluene (32 mL). The vessel was placed on a Parr shaker and pressurized to 50 psi (3.5 Kg/cm²) hydrogen. After shaking for one hour, more catalyst (3.0 g) and toluene (15 mL) were added and the vessel was pressurized to 50 psi (3.5 Kg/cm²) hydrogen and shaking continued. The reaction was judged to be complete after one hour. The catalyst was removed by filtration through fluted paper. The filter cake was washed with toluene (50 mL) and the filtrates were combined. The volatiles were removed under reduced pressure to afford N-(4-{[tert-butyl(dimethyl)silyl]oxy}butyl)quinoline-3,4-diamine (5.57 g, 16.11 mmol) as a dark oil. The material was used without further purification.

Part D

A round bottom flask was charged with a magnetic stir bar, N-(4-{[tert-butyl(dimethyl)silyl]oxy}butyl)quinoline-3,4-diamine (5.57 g, 16.11 mmol), trimethyl orthovalerate (5.23 g, 32.22 mmol) and toluene (47 mL). The reaction was heated to maintain a reflux that brought about a slow distillation to facilitate removal of the methanol byproduct. The reaction was judged to be complete after 15 hours at reflux. The reaction was cooled and the volatiles were removed under reduced pressure to afford of 2-butyl-1-(4-{[tert-butyl(dimethyl)silyl]oxy}butyl)-1H-imidazo[4,5-c]quinoline (4.65 g, 11.30 mmol) as a thick, dark brown oil. The material was used without further purification. MS (CI) for $C_{24}H_{37}N_3OSi$ m/z 412 (MH+), 298.

Part E

A round bottom flask was charged with a magnetic stir bar, 2-butyl-1-(4-{[tert-butyl(dimethyl)silyl]oxy}butyl)-1H-imidazo[4,5-c]quinoline (4.65 g, 11.30 mmol) and chloroform (57 mL). Solid 3-chloroperbenzoic acid (2.78 g, 12.43 mmol) was added portion wise to the solution over 15 minutes and the reaction was stirred at ambient temperature for 1 hour. More 3-chloroperbenzoic acid (0.5 g, 2.9 mmol) was added and after 30 minutes the starting material was completely consumed. The solution was partitioned between chloroform and aqueous saturated sodium bicarbonate. The layers were separated. The organic layer was washed with saturated aqueous sodium bicarbonate and brine, dried over anhydrous sodium sulfate, filtered and then concentrated under reduced pressure to afford 2-butyl-1-(4-{[tert-butyl(dimethyl)silyl]oxy}butyl)-1H-imidazo[4,5-c]quinoline-5N-oxide (4.83 g, 11.30 mmol) as a dark oil. The material was used without further purification.

Part F

A round bottom-flask was charged with a magnetic stir bar, 2-butyl-1-(4-{[tert-butyl(dimethyl)silyl]oxy}butyl)-1H-imidazo[4,5-c]quinoline-5N-oxide (11.30 mmol) and anhydrous dimethyl formamide (57 mL) under a nitrogen atmosphere. Phosphorus oxychloride (1.91 g, 12.43 mmol) was added to the reaction mixture in a drop wise fashion to give a homogeneous solution after complete addition. The reaction was judged to be complete after stirring for 1.5 hours at ambient temperature and was then partitioned between dichloromethane and saturated aqueous sodium bicarbonate. The layers were separated and the organic portion was washed with aqueous saturated sodium bicarbonate and brine, dried over anhydrous sodium sulfate, filtered and then concentrated under reduced pressure to afford 2-butyl-4-chloro-1-(4-chlorobutyl)-1H-imidazo[4,5-c]quinoline (3.65 g, 10.42 mmol) as a dark brown solid. The material was used without further purification. MS (CI) for $C_{18}H_{21}Cl_2N_3$ m/z 350 (MH$^+$); 314.

Part G

A round bottom flask was charged with a magnetic stir bar, 2-butyl4-chloro-1-(4-chlorobutyl)-1H-imidazo[4,5-c]quinoline (1.18 g, 3.37 mmol), benzenethiol (0.56 g, 5.05 mmol), triethylamine (0.68 g, 6.74 mmol), and dimethyl formamide (15 mL) under a nitrogen atmosphere. The reaction mixture was heated to 80° C. to give a homogeneous solution that was maintained at 80° C. for 2.5 hours. HPLC analysis indicated no starting material and a 3:1 mixture of 2-butyl4-chloro-1-[4-(phenylthio)butyl]-1H-imidazo[4,5-c]quinoline and 2-butyl4-(phenylthio)-1-[4-(phenylthio)butyl]-1H-imidazo[4,5-c]quinoline. The solution was cooled and then partitioned between ethyl acetate and aqueous saturated sodium bicarbonate. The layers were separated and the organic layer was washed with aqueous saturated sodium bicarbonate and brine, dried over anhydrous sodium sulfate, filtered and then concentrated under reduced pressure to afford a 3:1 mixture of the products named above (1.43 g). The material was used without further purification.

Part H

A 3:1 mixture of 2-butyl-4-chloro-1-[4-(phenylthio)butyl]-1H-imidazo[4,5-c]quinoline to 2-butyl-4-(phenylthio)-1-[4-(phenylthio)butyl]-1H-imidazo[4,5-c]quinoline (1.38 g) and a solution of 7% ammonia in methanol (30 mL) were combined in a bomb and heated to 150° C. The reaction was judged to be complete after 5 hours. The volatiles were removed under reduced pressure and the resulting residue was stirred in water and made basic (pH 10) with solid sodium carbonate. The aqueous mixture was extracted with chloroform (3×). The combined organic layers were washed with saturated aqueous sodium bicarbonate and brine, dried over anhydrous sodium sulfate, filtered and then concentrated under reduced pressure to afford a yellow crystalline solid. The solid (0.8 g) was dissolved in ethyl acetate (50 mL) and brought to reflux. Activated charcoal (0.4 g) was added; the resulting mixture was heated at reflux for 5 minutes and then the charcoal was removed by filtration through fluted paper to provide a colorless solution. The solution was concentrated under reduced pressure to give a solid that was recrystallized from ethyl acetate and hexanes to provide 2-butyl-1-[4-(phenylthio)butyl]-1H-imidazo[4,5-c]quinolin-4-amine (0.51 g, 1.25 mmol) as white needles, m.p. 118–120° C.

Analysis. Calculated for $C_{24}H_{28}N_4S$: % C 71.25; % H, 6.98; % N, 13.85. Found % C 71.12; % H, 6.81; % N, 13.62.

$^1$H-NMR (300 MHz, DMSO) δ 8.02 (d, J=8.3 Hz, 1H), δ 7.61 (d, J=8.3 Hz, 1H), δ 7.41 (t, J=8.3 Hz, 1H), δ 7.16–7.30 (m, 6H), δ 6.46 (bs, 2H), δ 4.52 (t, J=7.6 Hz, 2H), δ 3.02 (t, J=7.3 Hz, 2H), δ 2.89 (t, J=7.8 Hz, 2H), δ 1.95 (m, 2H), δ 1.75 (m, 4H), δ1.43 (sextet, J=7.3 Hz, 2H), δ 0.94 (t, J=7.3 Hz, 3H)

MS (CI) for $C_{24}H_{28}N_4S$ m/z 405 (MH$^+$), 282, 241

EXAMPLE 2

2-butyl-1-[2-(phenylthio)ethyl]-6,7,8,9-tetrahydro-1H-imidazo[4,5-c]quinolin-4-amine hydrochloride

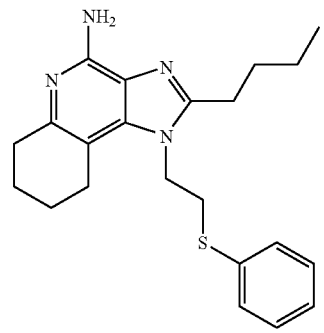

Part A

A round bottom flask was charged with a magnetic stir bar, 2-(4-amino-2-butyl-6,7,8,9-tetrahydro-1H-imidazo[4,5-c]quinolin-1-yl)ethanol (1.0 g, 3.47 mmol), tert-butyldimethylsilyl chloride (1.62 g, 10.75 mmol), triethylamine (1.58 g, 15.62 mmol), 4-dimethylaminopyridine (0.1 g), and chloroform (30 mL) to give a heterogeneous reaction mixture. The reaction was judged to be complete after stirring at 60° C. for 2 hours. The solution was partitioned between ethyl acetate and saturated aqueous ammonium chloride. The layers were separated and the organic layer was washed with aqueous saturated sodium bicarbonate and brine, dried over anhydrous sodium sulfate, filtered and then concentrated under reduced pressure to afford a 3:1 mixture of 2-butyl-1-(2-{[tert-butyl(dimethyl)silyl]oxy}ethyl)-6,7,8,9-tetrahydro-1H-imidazo[4,5-c]quinolin-4-amine and 2-butyl-N-[tert-butyl(dimethyl)silyl]-1-(2-{[tert-butyl(dimethyl)silyl]oxy}ethyl)-6,7,8,9-tetrahydro-1H-imidazo[4,5-c]quinolin-4-amine (1.79 g) as a dark brown oil. The material was used without further purification.

Part B

A round bottom flask was charged with a magnetic stir bar, a 3:1 mixture of 2-butyl-1-(2-{[tert-butyl(dimethyl)silyl]oxy}ethyl)-6,7,8,9-tetrahydro-1H-imidazo[4,5-c]quinolin-4-amine and 2-butyl-N-[tert-butyl(dimethyl)silyl]-1-(2-{[tert-butyl(dimethyl)silyl]oxy}ethyl)-6,7,8,9-tetrahydro-1H-imidazo[4,5]quinolin-4-amine (1.6 g) and a 1 M solution of acetic acid in dichloromethane (85 mL) to provide a homogenous solution. The reaction was judged to be complete after stirring at ambient temperature for 30 minutes. The solution was partitioned between chloroform and brine. The layers were separated and the organic layer was washed with aqueous saturated sodium bicarbonate and brine, dried over anhydrous sodium sulfate, filtered and then concentrated under reduced pressure to afford a dark brown oil. The material was purified by chromatography over silica gel (95/4/1 dichloromethane/methanol/ammonium hydroxide [14.8 M in water]) to provide 2-butyl-1-(2-{[tert-butyl(dimethyl)silyl]oxy}ethyl)-6,7,8,9-tetrahydro-1H-imidazo[4,5-c]quinolin-4-amine (1.24 g, 3.10 mmol) as a colorless oil.

Part C

A round bottom flask was charged with a magnetic stir bar, 2-butyl-1-(2-{[tert-butyl(dimethyl)silyl]oxy}ethyl)-6,7, 8,9-tetrahydro-1H-imidazo[4,5-c]quinolin-4-amine (0.83 g, 2.06 mmol), di-tert-butyl dicarbonate (1.79 g, 8.24 mmol), triethylamine (0.52 g, 5.15 mmol), 4-dimethylaminopyridine (0.1 g), and anhydrous tetrahydrofuran (21 mL) under a nitrogen atmosphere. The reaction mixture was heated to 60° C. to give a homogeneous solution that was maintained at 60° C. for 2.5 hours at which time the reaction was judged to be complete. The solution was cooled to ambient temperature and a 1 M solution of tetrabutylammonium fluoride in tetrahydrofuran (2.27 mL, 2.27 mmol) was added. The reaction was judged to be complete after stirring at ambient temperature for 30 minutes. The solution was partitioned between ethyl acetate and saturated aqueous ammonium chloride. The layers were separated. The organic layer was washed with saturated aqueous sodium bicarbonate and brine, dried over anhydrous sodium sulfate, filtered and then concentrated under reduced pressure to afford a light yellow solid. The material was purified by chromatography over silica gel (95/5 dichloromethane/methanol) to provide di(tert-butyl) 2-butyl-1-(2-hydroxyethyl)-6,7,8,9-tetrahydro-1H-imidazo[4,5-c]quinolin-4-ylimidodicarbonate. (0.55 g, 1.13 mmol) as a clear gum.

Part D

A round bottom flask was charged with a magnetic stir bar, di(tert-butyl) 2-butyl-1-(2-hydroxyethyl)-6,7,8,9-tetrahydro-1H-imidazo[4,5-c]quinolin-4-ylimidodicarbonate (0.55 g, 1.13 mmol) and anhydrous dichloromethane (11 mL) under a nitrogen atmosphere. The resulting homogeneous solution was cooled to −10° C. in a methanol/ice bath. To the cooled solution was added triethylamine (0.23 g, 2.26 mmol) and methanesulfonyl chloride (0.19 g, 1.70 mmol). The reaction was judged to be complete after stirring at −10° C. for 15 minutes and was then partitioned between ethyl acetate and saturated aqueous ammonium chloride. The layers were separated. The organic layer was washed with saturated aqueous sodium bicarbonate and brine, dried over anhydrous sodium sulfate, filtered and then concentrated under reduced pressure to afford 2-{4-[bis(tert-butoxycarbonyl)amino]-2-butyl-6,7,8,9-tetrahydro-1H-imidazo[4,5-c]quinolin-1-yl}ethyl methanesulfonate (0.61 g, 1.08 mmol) as a gummy yellow solid. The material was used without further purification. MS (CI) for $C_{27}H_{42}N_4O_7S$ m/z 567 (MH$^+$), 467, 367, 271.

Part E

A round bottom flask was charged with a magnetic stir bar, 2-{4-[bis(tert-butoxycarbonyl)amino]-2-butyl-6,7,8,9-tetrahydro-1H-imidazo[4,5-c]quinolin-1-yl}ethyl methanesulfonate (0.61 g, 1.08 mmol), benzenethiol (0.21 g, 1.88 mmol), triethylamine (0.25 g, 2:43 mmol) and anhydrous dimethyl formamide (11 mL) under a nitrogen atmosphere. The reaction mixture was heated to 80° C. to give a dark yellow, homogeneous solution that was maintained at 80° C. for 2.5 hours at which time the reaction was judged to be complete. The solution was cooled and then partitioned between ethyl acetate and saturated aqueous sodium bicarbonate. The layers were separated. The organic layer was washed with saturated aqueous sodium bicarbonate and brine, dried over anhydrous sodium sulfate, filtered and then concentrated under reduced pressure to afford a yellow oil. The material was purified by chromatography over silica gel (95/5 dichloromethane/methanol) to provide di(tert-butyl) 2-butyl-1-[2-(phenylthio)ethyl]-6,7,8,9-tetrahydro-1H-imidazo[4,5-c]quinolin-4-ylimidodicarbonate (0.54 g, 0.93 mmol) as a light yellow oil. MS (CI) for $C_{32}H_{44}N_4O_4S$ m/z 581 (MH$^+$), 481, 381, 245.

Part F

A round bottom flask was charged with a magnetic stir bar, di(tert-butyl) 2-butyl-1-[2-(phenylthio)ethyl]-6,7,8,9-tetrahydro-1H-imidazo[4,5-c]quinolin-4-ylimidodicarbonate (0.50 g, 0.86 mmol), a 4 M solution of hydrochloric acid in dioxane (5 mL), and dichloromethane (5 mL). The reaction was judged to be complete after stirring at ambient temperature for 2 hours. The volatiles were removed under reduced pressure to afford an off white solid. The material was recrystallized from acetonitrile to provide 2-butyl-1-[2-(phenylthio)ethyl]-6,7,8,9-tetrahydro-1-H-imidazo[4,5-c]quinolin-4-amine hydrochloride (0.17 g, 1.30 mmol) as fluffy white needles, m.p. 237–238° C. Analysis. Calculated for $C_{22}H_{28}N_4S.((H_2O)_{1/4}.(HCl)_2)$: % C 57.70; % H, 6.71; % N, 12.23. Found % C 57.62; % H, 6.57; % N, 12.41.

$^1$H-NMR (300 MHz, DMSO) δ 7.81 (bs, 2H), δ 7.22–7.39 (m, 5H), δ 4.64 (t, J=6.8 Hz, 2H), δ 3.40 (t, J=6.8 Hz, 2H), δ 2.75 (m, 6H), δ 1.71 (m, 6H), δ 1.34 (sexet, J=7.3 Hz, 2H), δ 0.89 (t, J=7.3 Hz, 3H)

MS (CI) for $C_{22}H_{28}N_4S$ $(H_2O)_{1/4}$ $(HCl)_2$ m/z 381 (MH$^+$), 245, 137

EXAMPLE 3

2-butyl-1-[4-(phenylsulfonyl)butyl]-1H-imidazo[4,5-c]quinolin-4-amine

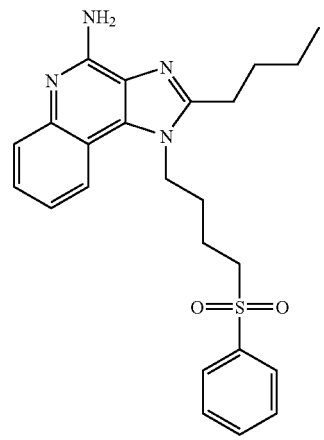

Part A

Using the general method of Example 1 Part E 2-butyl-1-(4-{[tert-butyl(dimethyl)silyl]oxy}butyl)-1H-imidazo[4,5-c]quinoline (16.0 g, 38. 87 mmol) was oxidized to 2-butyl-1-(4-{[tert-butyl(dimethyl)silyl]oxy}butyl)-1H-imidazo[4,5-c]quinoline-5N-oxide (16.61 g, 38.87 mmol) which was isolated without purification as a tan solid.

Part B

A round bottom flask was charged with a magnetic stir bar, 2-butyl-1-(4-{[tert-butyl(dimethyl)silyl]oxy}butyl)-1H-imidazo[4,5-c]quinoline-5N-oxide (16.61 g, 38.87 mmol), a 14.8 M solution of ammonium hydroxide in water (75 mL) and chloroform (200 mL). To the rapidly stirring solution was added p-toluenesulfonyl chloride (8.15 g, 42.76 mmol) in a portion wise fashion resulting in a mild exotherm. The reaction was judged to be complete after stirring at ambient temperature for 10 minutes. The solution was partitioned between chloroform and aqueous saturated sodium bicarbonate. The layers were separated. The organic layer was washed with saturated aqueous sodium bicarbonate and brine, dried over anhydrous sodium sulfate, filtered and then concentrated under reduced pressure to afford an off-white solid. The material was triturated with ethyl ether and collected by filtration to provide 2-butyl-1-(4-{[tert-butyl(dimethyl)silyl]oxy}butyl)-1H-imidazo[4,5-c]quinolin-4-amine (9.3 g, 21.80 mmol) as a fine white powder. The material was used without further purification.

Part C

A round bottom flask was charged with a magnetic stir bar, 2-butyl-1-(4-{[tert-butyl(dimethyl)silyl]oxy}butyl)-1H-imidazo[4,5-c]quinolin-4-amine (9.2 g, 21.56 mmol), a 1M solution of tetrabutylammonium fluoride in tetrahydrofuran (23.72 mL, 23.72 mmol), and anhydrous tetrahydrofuran (100 mL) to give a homogeneous, light orange solution. The reaction was judged to be complete after stirring at ambient temperature for 1 hour. While stirring, water (100 mL) was added and resulted in a mild exotherm. The volatiles were removed under reduced pressure until a solid precipitated out of solution. The solid was collected by filtration and washed with water (20 mL) and acetone (20 mL) to afford a white solid. The material was triturated with ethyl ether (50 mL) and collected by filtration to provide 4-(4-amino-2-butyl-1H-imidazo[4,5-c]quinolin-1-yl)butan-1-ol (6.12 g, 19.59 mmol) as a fine white solid, m.p. 184–186° C.

Analysis. Calculated for $C_{18}H_{24}N_4O$: % C 69.20; % H, 7.74; % N, 17.93. Found % C 69.05; % H, 8.02; % N, 18.03.

MS (CI) for $C_{18}H_{24}N_4O$ m/z 313((MH$^+$)

Part D

A round bottom flask was charged with a magnetic stir bar, 4-(4-amino-2-butyl-1H-imidazo[4,5-c]quinolin-1-yl)butan-1-ol (7.3 g, 23.37 mmol), triethylamine (3.55 g, 35.06 mmol), and anhydrous dimethyl formamide (93 mL) under a nitrogen atmosphere. To the stirred solution was added phosphorus oxychloride (3.94 g, 25.70 mmol) in a drop wise fashion resulting in an exotherm to give a dark yellow heterogeneous reaction mixture. The reaction mixture was heated to 60° C. to give a homogeneous solution that was maintained at 60° C. for 5 hours at which time the starting material was completely consumed. The volatiles were removed under reduced pressure to give a dark brown oil. The material was partitioned between chloroform and saturated aqueous sodium bicarbonate. The layers were separated and the aqueous layer was extracted with chloroform (1×). The organic layers were combined and the volatiles removed under reduced pressure to afford a 2:1 mixture of N-[2-butyl-1-(4-chlorobutyl)-1H-imidazo[4,5-c]quinolin-4-yl]-N,N-dimethylimidoformamide and 2-butyl-1-(4-chlorobutyl)-1H-imidazo[4,5-c]quinolin-4-amine (7.70 g) as an off-white solid. The material was used without further purification.

Part E

A round bottom flask was charged with a magnetic stir bar, a 2:1 mixture of N'-[2-butyl-1H-(4-chlorobutyl)-1H-imidazo[4,5-c]quinolin-4-yl]-N,N-dimethylimidoformamide and 2-butyl-1-(4-chlorobutyl)-1H-imidazo[4,5-c]quinolin-4-amine (1.3 g), benzenesulfinic acid sodium salt (1.67 g, 10.11 mmol), and anhydrous dimethyl formamide (15 mL) under a nitrogen atmosphere. The resulting solution was heated to 100° C. to give a homogeneous solution that was maintained at 100° C. for 90 hours at which time the starting materials were completely consumed. The solution was cooled and then partitioned between chloroform and water. The layers were separated. The organic layer was washed with saturated aqueous sodium bicarbonate and brine, dried over anhydrous sodium sulfate, filtered and then concentrated under reduced pressure to afford a dark yellow gum. The material was dissolved in methanol (20 mL) and a 4 M solution of hydrochloric acid in dioxane (3.02 mL, 12.1 mmol). The light orange solution was stirred at ambient temperature for 12 hours at which time the reaction was judged to be complete. The volatiles were removed under reduced pressure to give a light yellow gum. The material was partitioned between chloroform and saturated aqueous sodium bicarbonate. The layers were separated and the aqueous layer was extracted with chloroform (1×). The organic layers were combined, washed with brine, dried over anhydrous sodium sulfate, filtered and then concentrated under reduced pressure to afford a light yellow solid. The material was purified by chromatography over silica gel (95/5 dichloromethane/methanol) to give an off-white solid. The solid (0.63 g) was dissolved in ethyl acetate (50 mL) and brought to reflux. Activated charcoal (0.6 g) was added and the resulting mixture was heated at reflux for 5 minutes. The charcoal was removed by filtration through fluted paper to provide a colorless solution. The solution was concentrated under reduced pressure to give a solid that was recrystallized from ethyl acetate and hexanes to provide 2-butyl-1-[4-(phenylsulfonyl)butyl]-1H-imidazo[4,5-c]quinolin-4-amine (0.37 g, 0.85 mmol) as a white fluffy solid, m.p. 179–180° C. Analysis. Calculated for $C_{24}H_{28}N_4O_2S$: % C 66.03; % H, 6.46; % N, 12.83. Found % C 65.88; % H, 6.49; % N, 12.76.

$^1$H-NMR (300 MHz, DMSO) δ 7.98 (d, J=8.3 Hz, 1H), δ 7.82 (m, 2H) δ 7.73 (d, J=7.3 Hz, 1H), δ 7.62 (m, 3H) δ 7.41 (t, J=7.6 Hz, 1H), δ 7.22 (t, J=7.6 Hz, 1H), δ 6.45 (bs, 2H), δ 4.51 (t, J=7.3 Hz, 2H), δ 3.90 (t, J=7.8 Hz, 2H), δ 2.86 (t, J=7.6 Hz, 3H), δ 1.69–1.90 (m, 6H), δ 1.43 (sextet, J=7.3 Hz, 2H), δ 0.95 (t, J=7.3 Hz, 3H)

MS (CI) for $C_{24}H_{28}N_4O_2S$ m/z 437 ((MH$^+$), 295

EXAMPLE 4

2-butyl-1-[4-(methylthio)butyl]-1H-imidazo[4,5-c]quinolin-4-amine

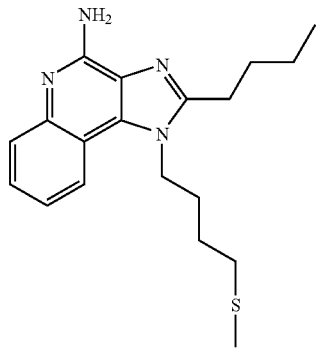

Part A

A round bottom flask was charged with a magnetic stir bar, a 2:1 mixture of N'-[2-butyl-1-(4-chlorobutyl)-1H-imidazo[4,5-c]quinolin-4-yl]-N,N-dimethylimidoformamide and 2-butyl-1-(4-chlorobutyl)-1H-imidazo[4,5-c]quinolin-4-amine (6.17 g), a 4 M solution of hydrochloric acid in dioxane (21.15 mL, 84.56 mmol), and methanol (200 mL) to provide a light orange solution. The reaction was judged to be complete after stirring at ambient temperature for 43 hours. The volatiles were removed under reduced pressure and the resulting light yellow solid was partitioned between chloroform and saturated aqueous sodium bicarbonate. The layers were separated and the aqueous layer was extracted with chloroform (1×). The organic layers were combined, dried over anhydrous sodium sulfate, filtered and then concentrated under reduced pressure to afford 2-butyl-1-(4-chlorobutyl)-1H-imidazo[4,5-c]quinolin-4-amine (4.65 g, 14.05 mmol) as an off-white solid. The material was used without further purification. MS (CI) for $C_{18}H_{23}ClN_4$ m/z 331 (MH+), 295.

Part B

A round bottom flask was charged with a magnetic stir bar, 2-butyl-1-(4-chlorobutyl)-1H-imidazo[4,5-c]quinolin-4-amine (1.5 g, 4.53 mmol), sodium thiomethoxide (0.48 g, 6.80 mmol), and anhydrous dimethyl formamide (18 mL) under a nitrogen atmosphere. The reaction mixture was heated to 60° C. to give a homogeneous solution that was maintained at 60° C. for 16 hours at which time the starting material was completely consumed. The solution was cooled and then partitioned between chloroform and water. The layers were separated and the organic layer was washed with saturated aqueous sodium bicarbonate. The combined aqueous layers were extracted with chloroform (1×). The combined organic layers were washed with brine, dried over anhydrous sodium sulfate, filtered and then concentrated under reduced pressure to afford a dark brown oil. The material was purified by chromatography over silica gel (90/10 dichloromethane/methanol) to provide a light yellow solid. The solid was recrystallized from dimethyl formamide and water to give 2-butyl-1-[4-(methylthio)butyl]-1H-imidazo[4,5-c]quinolin-4-amine (0.83 g, 2.42 mmol) as light yellow needles, m.p. 127–130° C.

Analysis. Calculated for $C_{19}H_{26}N_4S$: % C 66.63; % H, 7.65; % N, 16.36. Found % C 66.68; % H, 7.53; % N, 16.35.

$^1$H-NMR (500 MHz, DMSO) δ 8.04 (d, J==8.3 Hz, 1H), δ 7.61 (d, J=8.3 Hz, 1H), δ 7.41 (t, J=8.3 Hz, 1H), δ 7.25 (t, J=8.3 Hz, 1H), δ 6.43 (bs, 2H), δ 4.52 (t, J=7.6 Hz, 2H), δ 2.92 (t, J=7.8 Hz, 2H), δ 2.53 (t, J=7.3 Hz, 2H), δ 2.01 (s, 3H), δ 1.90 (m, 2H), δ 1.80 (p, J=7.8 Hz, 2H) δ 1.71 (p, J=7.3 Hz, 2H) δ 1.46 (sextet, J=7.3 Hz, 2H), δ 0.96 (t, J=7.3 Hz, 3H)

MS (CI) for $C_{19}H_{26}N_4S$ m/z 343 (MH+), 295, 241

EXAMPLE 5

2-butyl-1-[4-(methylsulfonyl)butyl]-1H-imidazo[4,5-c]quinolin-4-amine

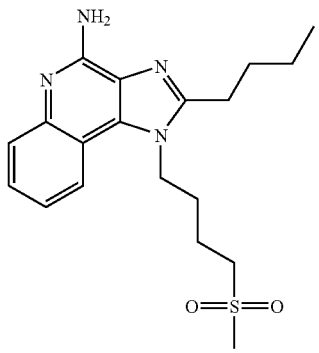

Part A

A round bottom flask was charged with a magnetic stir bar, 2-butyl-1-[4-(methylthio)butyl]-1H-imidazo[4,5-c]quinolin-4-amine (1.2 g, 3.50 mmol), and chloroform (18 mL). Solid 3-chloroperbenzoic acid (1.72 g 7.71 mmol) was added to the resulting solution portion wise over 15 minutes. The reaction was judged to be complete after stirring at ambient temperature for 5 minutes. The solution was partitioned between chloroform and 1% aqueous sodium carbonate. The layers were separated and the organic layer was washed with brine, dried over anhydrous sodium sulfate, filtered and then concentrated under reduced pressure to afford a light brown solid. The material was purified by chromatography over silica gel (90/10 dichloromethane/methanol to provide an off-white solid. The solid was recrystallized from acetonitrile and water to give 2-butyl-1-[4-(methylsulfonyl)butyl]-1H-imidazo[4,5-c]quinolin-4-amine (0.61 g, 1.63 mmol) as off-white needles, m.p. 164–165° C.

Analysis. Calculated for $C_{19}H_{26}N_4O_2S$: % C 60.94; % H, 7.00; % N 14.96. Found % C 60.71; % H, 6.94; % N, 14.94.

$^1$H-NMR (300 MHz, DMSO) δ 8.03 (d, J=8.3 Hz, 1H) δ 7.61 (d, J=8.3 Hz, 1H), δ 7.42 (t, J=8.3 Hz, 1H), 87.26 (t, J=8.3 Hz, 1H), δ 6.46 (s, 2H), δ 4.56 (t, J=7.6 Hz, 2H), δ 3.21 (t, J=7.3 Hz 2H), δ 2.96 (s, 3H), δ 2.93 (t, J=7.8 Hz, 2H), δ 1.91 (m, 4H), δ 1.81 (p, J=7.3 Hz, 2H), δ 1.45 (sextet, J=7.3 Hz, 2H), δ 0.96 (t, J=37.3 Hz, 3H)

MS (CI) for $C_{19}H_{26}N_4S$ m/z 375 (MH+), 295

EXAMPLE 6

1-[2-(phenylthio)ethyl]-1H-imidazo[4,5-c]quinolin-4-amine

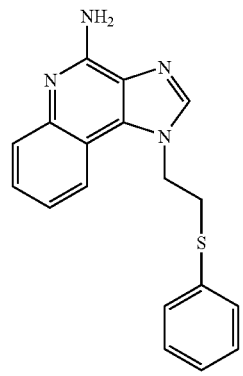

Part A

A round bottom flask was charged with a magnetic stir bar, 2-(4-amino-1H-imidazo[4,5-c]quinolin-1-yl)ethanol (8.46 g, 37.06 mmol), and thionyl chloride (68.99 g, 57.99 mmol) under a nitrogen atmosphere. The reaction mixture was heated to 80° C. to give a heterogeneous reaction mixture that was maintained at 80° C. for 2 hours at which time the starting material was completely consumed. The solution was cooled and quenched by the addition of water (400 mL). To the stirred solution was added solid sodium carbonate until the pH reached 10 at which time a solid precipitated out of solution. The solid was collected by filtration to afford 1-(2-chloroethyl)-1H-imidazo[4,5-c]quinolin-4-amine (7.86 g, 31.86 mmol) as an off-white solid. The material was used without further purification.

Part B

A round bottom flask was charged with a magnetic stir bar, 1-(2-chloroethyl)-1H-imidazo[4,5-c]quinolin-4-amine (2.0 g, 8.11 mmol), sodium benzenethiolate (1.79 g, 12.16 mmol) and anhydrous dimethyl sulfoxide (40 mL) under a nitrogen atmosphere. The reaction mixture was heated to 100° C. to give a homogeneous solution that was maintained at 100° C. for 30 minutes at which time the starting material was completely consumed. The hot solution was poured into rapidly stirred water (300 mL) which caused a solid to precipitate out of solution. The solid was collected by filtration to afford an off-white solid. The material was triturated with acetonitrile and collected by filtration to give 1-[2-(phenylthio)ethyl]-1H-imidazo[4,5-c]quinolin-4-amine (2.08 g, 6.49 mmol) as an off-white powder, m.p.233–235° C.

Analysis. Calculated for $C_{18}H_{16}N_4S$: % C 67.47; % H, 5.03; % N, 17.49. Found: % C 67.20; % H, 4.95; % N, 17.52.

$^1$H-NMR (300 MHz, DMSO) δ 8.14 (s, 1H), δ 7.76 (d, J=8.3 Hz, 1H), δ 7.60 (t, J=8.3 Hz, 1H), δ 7.28–7.44 (m, 6H), δ 7.12 (t, J=8.3 Hz, 1H), δ 6.58 (bs, 2H), δ 4.79 (t, J=6.8 Hz, 2H), 3.48 (t, 6.8 Hz, 2H).

MS (CI) for $C_{18}H_{16}N_4S$ m/z 321 (MH$^+$), 185, 137

EXAMPLE 7

1-[4-(phenylsulfonyl)butyl]-1H-imidazo[4,5-c]quinolin-4-amine

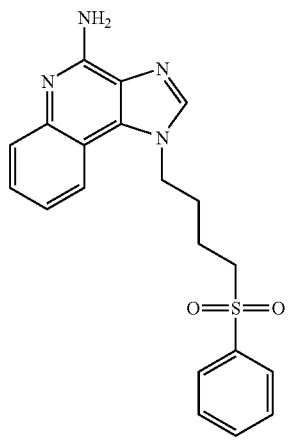

Part A

A round bottom flask was charged with a magnetic stir bar, N,N-dibenzyl-1H-imidazo[4,5-c]quinolin-4-amine (20.0 g, 55.04 mmol), sodium hydride (3.3 g, 60% dispersion, 82.56 mmol), and anhydrous dimethyl formamide (275 mL) under a nitrogen atmosphere. After the reaction mixture had stirred at ambient temperature for 2 hours, 4-chloro-1-iodobutane (19.23 g, 88.06 mmol) was added and the resulting homogeneous solution was stirred at ambient temperature for 48 hours at which time the starting material was consumed. The solution was partitioned between ethyl acetate and water. The layers were separated and the organic layer was washed with saturated aqueous sodium bicarbonate and brine, dried over anhydrous sodium sulfate, filtered and then concentrated under reduced pressure to afford a light yellow solid. The material was recrystallized from ethyl acetate and hexanes to give N,N-benzyl-1-(4-chlorobutyl)-1H-imidazo[4,5-c]quinolin-4-amine (20.7 g, 45.49 mmol) as white needles. MS (CI) for $C_{28}H_{27}ClN_4$ m/z 455 (MH$^+$), 365, 329, 239

Part B

A round bottom flask was charged with a magnetic stir bar, N,N-dibenzyl-1-(4-chlorobutyl)-1H-imidazo[4,5-c]quinolin-4-amine (7.0 g, 15.38 mmol), sodium benzenethiolate (3.46 g, 26.15 mmol), and anhydrous dimethyl formamide (77 mL) under a nitrogen atmosphere. The reaction mixture was heated to 60° C. to give a heterogeneous mixture that was maintained at 60° C. for 4 hours at which time the starting material was completely consumed. The cooled solution was partitioned between ethyl acetate and water. The layers were separated. The organic layer was washed with saturated aqueous sodium bicarbonate and brine, dried over anhydrous sodium sulfate, filtered and then concentrated under reduced pressure to afford a colorless oil. The material was purified by chromatography over silica gel (80/20 hexanes/ethyl acetate) to provide N,N-dibenzyl-1-[4-(phenylthio)butyl]-1H-imidazo[4,5-c]quinolin-4-amine (7.5 g, 14.19 mmol) as a colorless oil. MS (CI) for $C_{34}H_{32}N_4S$ m/z 529 (MH$^+$), 439, 349

Part C

A round bottom flask was charged with a magnetic stir bar, N,N-dibenzyl-1-[4-(phenylthio)butyl]-1H-imidazo[4,5-c]quinolin-4-amine (3.64 g, 6.88 mmol) and chloroform (34 mL). Solid 3-chloroperbenzoic acid (3.39 g, 15.14 mmol) was added portion wise to the resulting solution over 5 minutes. The reaction was judged to be complete after stirring at ambient temperature for 5 minutes. The solution was partitioned between chloroform and 1% aqueous sodium carbonate. The layers were separated. The organic layer was washed with brine, dried over anhydrous sodium sulfate, filtered and then concentrated under reduced pressure to afford a red gum. The material was purified by chromatography over silica gel (dichloromethane) to provide N,N-dibenzyl-1-[4-(phenylsulfonyl)butyl]-1H-imidazo[4,5-c]quinolin-4-amine (2.85 g, 5.08 mmol) as a light pink gum. MS (CI) for $C_{34}H_{32}N_4O_2S$ m/z 561 (MH$^+$), 471, 381

Part D

A round bottom flask was charged with a magnetic stir bar, N,N-dibenzyl-1-[4-(phenylsulfonyl)butyl]-1H-imidazo[4,5-c]quinolin-4-amine (1.0 g, 1.78 mmol), triflic acid (2.68 g, 17.83 mmol), and anhydrous dichloromethane (14 mL) under a nitrogen atmosphere. The reaction was judged to be complete after stirring at ambient temperature for 24 hours. The solution was partitioned between chloroform and excess aqueous sodium hydroxide (20%). The layers were separated. The aqueous layer was extracted with chloroform (3×). The organic layers were combined and then concentrated under reduced pressure to afford a light brown solid. The material was purified by chromatography over silica gel (90/10 dichloromethane/methanol) to provide a fine white powder which was recrystallized from acetonitrile to give 1-[4-(phenylsulfonyl)butyl]-1H-imidazo[4,5-c]quinolin-4-amine (0.32 g, 0.84 mmol) as white needles, m.p. 175–177° C.

Analysis. Calculated for $C_{20}H_{20}N_4O_2S$: % C 63.14; % H, 5.30; % N, 14.73. Found: % C 63.14; % H, 5.24; % N, 14.77.

$^1$H-NMR (300 MHz, DMSO) δ 8.15 (s, 1H), δ 8.01 (d, J=8.3 Hz, 1H), δ 7.80 (m, 2H), δ 7.71 (m, 1H), δ 7.60 (m, 3H), δ 7.44 (t, J=8.3 Hz, 1H), δ 7.24 (t, J=8.3 Hz, 1H), δ 6.59 (bs, 2H), δ 4.59 (t, J=6.8 Hz, 2H), δ 3.38 (t, J=7.8 Hz, 2H), δ 1.93 (m, 2H), δ 1.58 (m, 2H)

MS (CI) for $C_{20}H_{20}N_4O_2S$ m/z 381 (MH$^+$), 239

EXAMPLE 8

1-[4-(methylsulfonyl)butyl]-1H-imidazo[4,5-c]quinolin-4-amine

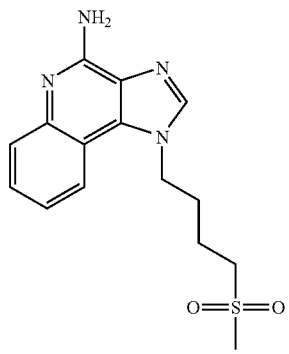

Part A

Using the general method of Example 7 Part B, N,N-dibenzyl-1-(4-chlorobutyl)-1H-imidazo[4,5-c]quinolin-4-amine (5.0 g, 10.99 mmol) was converted to N,N-dibenzyl-1-[4-(methylthio)butyl]-1H-imidazo[4,5-c]quinolin-4-amine using sodium thiomethoxide (1.16 g, 16.48 mmol). The material was purified by chromatography over silica gel (80/20 hexanes/ethyl acetate) to provide the product (4.91 g, 10.52 mmol) as a colorless oil. MS (CI) for $C_{29}H_{30}N_4S$ m/z 467 (MH$^+$), 377, 287, 185

Part B

Using the general method of Example 7 Part C, N,N-dibenzyl-1-[4-(methylthio)butyl]-1H-imidazo[4,5-c]quinolin-4-amine (4.91 g, 15.52 mmol) was oxidized to N,N-dibenzyl-1-[4-(methylsulfonyl)butyl]-1H-imidazo[4,5-c]quinolin-4-amine which was purified by chromatography over silica gel (80/20 hexanes/ethyl acetate) to provide the product (4.53 g, 9.08 mmol) as a light orange solid. MS (CI) for $C_{29}H_{30}N_4O_2S$ m/z 499 (MH$^+$), 409, 319

Part C

Using the general method of Example 7 Part D, N,N-dibenzyl-1-[4-(methylsulfonyl)butyl]-1H-imidazo[4,5-c]quinolin-4-amine (4.53 g, 9.08 mmol) was converted to 1-[4-(methylsulfonyl)butyl]-1H-imidazo[4,5-c]quinolin-4-amine. The material was recrystallized from methanol and water to afford the title compound (1.33 g, 4.18 mmol) as white needles, m.p. 203–204° C.

Analysis. Calculated for $C_{15}H_{18}N_4O_2S$: % C 56.58; % H, 5.70; % N, 17.60. Found: % C 56.33; % H, 5.63; % N, 17.41.

$^1$H-NMR (300 MHz, DMSO) δ 8.22 (s, 1H), δ 8.06 (d, J=8.3 Hz, 1H), δ 7.62 (d, J=8.3 Hz, 1H), δ 7.45 (t, J=8.3 Hz, 1H), δ 7.27 (t, J=8.3 Hz, 1H), δ 6.59 (bs, 2H), δ 4.65 (t, J=6.8 Hz, 2H), δ 3.19 (t, J=7.8 Hz, 2H), δ 2.93 (s, 3H), δ 1.99 (m, 2H), δ 1.74 (m, 2H)

MS (CI) for $C_{15}H_{18}N_4O_2S$ m/z 319 (MH$^+$), 239

EXAMPLE 9

1-[4-(phenylthio)butyl]-1H-imidazo[4,5-c]quinolin-4-amine

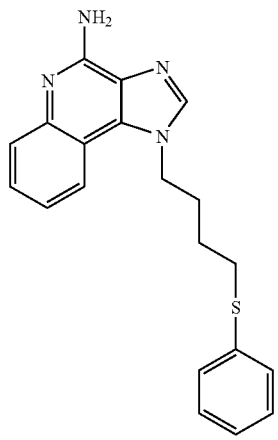

Part A

Using the general method of Example 1 Part D, N-(4-{[tert-butyl(dimethyl)silyl]oxy}butyl)quinoline-3,4-diamine (101.21 g, 292.90 mmol) was cyclized to 1-(4-{[tert-butyl(dimethyl)silyl]oxy}butyl)-1H-imidazo[4,5-c]quinoline using triethyl orthoformate (65.11 g, 439.35 mmol). The product (75.0 g, 210.93 mmol) was isolated as a brown oil and used without further purification.

Part B

Using the general method of Example 1 Part E, 1-(4-{[tert-butyl(dimethyl)silyl]oxy}butyl)-1H-imidazo[4,5-c]quinoline (42.2 g, 118.69 mmol) was oxidized to 1-(4-{([tert-butyl(dimethyl)silyl]oxy}butyl)-1H-imidazo[4,5-c]quinoline-5N-oxide (44.10 g, 118.69 mmol) which was isolated without further purification as a tan solid.

Part C

Using the general method of Example 3 Part B, 1-(4-{[tert-butyl(dimethyl)silyl]oxy}butyl)-1H-imidazo[4,5-c]quinoline-5N-oxide (44.10 g, 118.69 mmol) was aminated to provide 1-(4-{[tert-butyl(dimethyl)silyl]oxy}butyl)-1H-imidazo[4,5-c]quinolin-4-amine. The material was triturated with ethyl ether and collected by filtration to afford the product (21.54 g, 58.12 mmol) as a light brown solid which was used without further purification.

Part D

Using the general method of Example 3 Part C, 1(4-{[tert-butyl(dimethyl)silyl]oxy}butyl)-1H-imidazo[4,5-c]quinolin-4-amine (21.5 g, 58.02 mmol) was converted to 4-(4-amino-1H-imidazo[4,5-c]quinolin-1-yl butan-1-ol. The material was triturated with cold methanol (0° C.) and collected by filtration to afford the product (13.92 g, 54.30 mmol) which was used without further purification. MS (CI) for $C_{14}H_{16}N_4O$ m/z 257 (MH$^+$), 185

Part E

Using the general method of Example 6 Part A, 4-(4-amino-1H-imidazo[4,5-c]quinolin-1-yl)butan-1-ol (5.0 g, 19.51 mmol) was chlorinated to provide 1-(4-chlorobutyl)-1H-imidazo[4,5-c]quinolin-4-amine (4.92 g, 17.91 mmol) which was isolated without further purification as an off-white solid.

Part F

Using the general method of Example 6 Part B, except that the reaction temperature was lowered to 80° C., 1-(4-chlorobutyl)-1H-imidazo[4,5-c]quinolin-4-amine (1.5 g, 5.46 mmol) was converted to 1-[4-(phenylthio)butyl]-1H-imidazo[4,5-c]quinolin-4-amine. The resulting solid (1.53 g) was dissolved in acetonitrile (90 mL) and brought to reflux. Activated charcoal (0.9 g) was added and the resulting mixture was heated at reflux for 5 minutes and then the charcoal was removed by filtration through fluted paper to provide a colorless solution. The title compound (0.86 g, 2.47 mmol) was isolated as white needles, m.p 158–160° C.

Analysis. Calculated for $C_{20}H_{20}N_4S$: % C 68.94; % H, 5.79; % N, 16.08. Found: % C 68.70; % H, 5.74; % N, 16.08.

$^1$H-NMR (300 MHz, DMSO) δ 8.18 (s, 1H), δ 8.05 (d, J=8.3 Hz, 1H), δ 7.63 (d, J=8.3 Hz, 1H), δ 7.45 (t, J=8.3 Hz, 1H), δ 7.26 (m, 5H), δ 7.14–7.19 (m, 1H), δ (bs, 2H), δ 4.62 (t, J=6.8 Hz, 2H), δ 3.00 (t, J=7.3 Hz, 2H), δ 2.00 (m, 2H), δ 1.61 (m, 2H)

MS (CI) for $C_{20}H_{20}N_4S$ m/z 349 (MH$^+$), 185

EXAMPLE 10

1-[4-(methylthio)butyl]-1H-imidazo[4,5-c]quinolin-4-amine

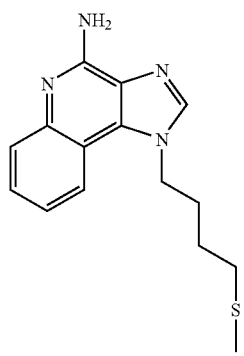

Part A

Using the general method of Example 6 Part B, except that the reaction temperatures was lowered to 80° C., 1-(4-chlorobutyl)-1H-imidazo[4,5-c]quinolin-4-amine (1.5 g, 5.46 mmol) was converted to 1-[4-(methylthio)butyl]-1H-imidazo[4,5-c]quinolin-4-amine using sodium thiomethoxide (0.88 g, 12.56 mmol) in lieu of sodium benzenethiolate. The resulting solid (1.26 g) was dissolved in acetonitrile (40 mL) and brought to reflux. Activated charcoal (0.7 g) was added, the resulting mixture was heated at reflux for 5 minutes and then the charcoal was removed by filtration through fluted paper to provide a colorless solution. The solution was concentrated under reduced pressure to give a solid that was recrystallized from acetonitrile. The title compound (0.66 g, 2.30 mmol) was isolated as white needles, m.p 163–164° C.

Analysis. Calculated for $C_{15}H_{18}N_4S$: % C 62.91; % H, 6.34; % N, 19.56. Found: % C 62.70; % H, 6.19; % N, 19.45.

$^1$H-NMR (300 MHz, DMSO) δ 8.21 (s, 1H), δ 8.06 (d, J=8.3 Hz, 1H), δ 7.62 (d, J=8.3 Hz, 1H), δ 7.44 (t, J=8.3 Hz, 1H), δ 7.26 (t, J=8.3 Hz, 1H), δ 6.59 (bs, 2H), δ 4.62 (t, J=7.6 Hz, 2H), δ 2.50 (t, J=6.8 Hz, 2H), δ 1.99 (s, 3H), δ 1.95 (p, J=7.3 Hz, 2H), δ 1.59 (p, J=73 Hz, 2H)

MS (CI) for $C_{15}H_{18}N_4S$ m/z 287 (MH$^-$), 185

EXAMPLE 11

2-butyl-1-[5-(methylsulfonyl)pentyl]-1H-imidazo[4.5-c]quinolin-4-amine

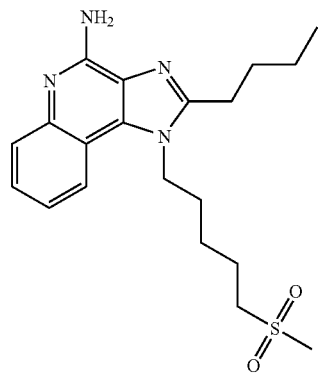

Part A

Using the general method of Example 1 Part A, 4-chloro-3-nitroquinoline (107.7 g, 525.87 mmol) was converted to 5-[(3 nitroqunolin-4-yl)amino]pentan-1-ol using 5-amino-1-pentanol (79.82 g, 788.81 mmol) in lieu of 4-amino-butanol. The product (117.22 g, 425.77 mmol) was used without further purification as a dark yellow solid. MS (CI) for $C_{14}H_{17}N_3O_3$ m/z 276 (MH$^+$), 224

Part B

A round bottom flask was charged with a magnetic stir bar, 5-[(3-nitroquinolin-4-yl)amino]pentan-1-ol (5.0 g, 18.16 mmol), and thionyl chloride (40.78 g, 0.34 mmol) under a nitrogen atmospheres The reaction mixture was heated to 80° C. to give a homogeneous solution that was maintained at 80° C. for 1 hour at which time the starting material was completely consumed. The volatiles were removed under reduced pressure and the resulting oil stirred in water made basic (pH 10) with solid sodium carbonate. The resulting solid was collected by filtration to afford N-(5-chloropentyl)-3-nitroquinolin-4-amine (4.80 g, 16.34 mmol) which was used without further purification.

Part C

Using the general method of Example 6 Part B, except that the reaction temperature was lowered to 80° C., N-(5-chloropentyl)-3-nitroquinolin-4-amine (4.75 g, 16.17 mmol) was converted to N-[5-(methylthio)pentyl]-3-nitroquinolin-4-amine using sodium thiomethoxide (1.43 g, 19.40 mmol) in lieu of sodium benzenethiolate. The product (3.28 g, 10.74 mmol) was isolated without further purification as a light yellow solid. MS (CI) for $C_{15}H_{19}N_3O_2S$ m/z 306 (MH$^+$), 272, 117

Part D

Using the general method of Example 1 Part C, N-[5-(methylthio)pentyl]-3-nitroquinolin-4-amine (3.20 g, 10.48 mmol) was reduced to $N^4$-[5-(methylthio)pentyl]quinoline-3,4-diamine (2.89 g, 10.48 mmol) which was isolated without further purification as a brown oil.

Part E

Using the general method of Example 1 Part D, $N^4$-[5-(methylthio)pentyl]quinoline-3,4-diamine (2.89 g, 10.48 mmol) was cyclized to provide 2-butyl-1-[5-methylthio)pentyl]-1H-imidazo[4,5-c]quinoline. The material was purified by chromatography over silica gel (ethyl acetate) to afford the product (2.10 g, 6.15 mmol) as a light brown oil.

Part F

A round bottom flask was charged with a magnetic stir bar, 2-butyl-1-[5-(methylthio)pentyl]-1H-imidazo[4,5-c]quinoline (2.1 g, 6.15 mmol) and chloroform (31 mL). Solid 3-chloroperbenzoic acid (4.41 g, 19.68 mmol) was added portion wise to the solution over 10 minutes and the reaction was stirred at ambient temperature for 30 minutes at which time the starting material was completely consumed. The solution was partitioned between chloroform and saturated aqueous sodium bicarbonate. The layers were separated. The organic layer was washed with saturated aqueous sodium bicarbonate and brine, dried over anhydrous sodium sulfate, filtered and then concentrated under reduced pressure to afford 2-butyl-1-[5-(methylsulfonyl)pentyl]-1H-imidazo[4,5-c]quinoline-5N-oxide (2.40 g, 6.15 mmol) as a tan solid. The material was used without further purification.

Part G

Using the general method of Example 3 Part B, 2-butyl-1-[5-(methylsulfonyl)pentyl]-1H-imidazo[4,5-c]quinoline-5N-oxide (2.40 g, 6.15 mmol) was aminated to provide 2-butyl-1-[5-(methylsulfonyl)pentyl]-1H-imidazo[4,5-c]quinolin-4-amine. The resulting solid (2.24 g) was dissolved in acetonitrile (40 mL) and brought to reflux. Activated charcoal (1 g) was added and the resulting mixture was heated at reflux for 5 minutes and then the charcoal was removed by filtration through fluted paper to provide a light brown solution. Upon cooling 2-butyl-1-[5-(methylsulfonyl)pentyl]-1H-imidazo[4,5-c]quinolin-4-amine (0.90 g, 2.32 mmol) was isolated as white needles, m.p. 173–175° C.

Analysis. Calculated for $C_{20}H_{28}N_4O_2S$: % C 61.83; % H, 7.26; % N, 14.42. Found: % C 61.58; % H, 7.27; % N, 14.36.

$^1$H-NMR (300 MHz, DMSO) δ 8.01 (d, J=8.3 Hz, 1H), 7.61 (d, J=8.3 Hz, 1H), δ 7.41 (t, J=8.3 Hz, 1H), δ 7.26 (t, J=8.3 Hz, 1H), δ 6.45 (bs, 2H), δ 4.51 (t, J=7.6 Hz, 2H), δ 3.10 (t, J=7.8 Hz, 2H), δ 2.92 (s, 3H), δ 2.92 (t, J=7.3 Hz, 2H), δ 1.76 (m, 6H), δ 1.54 (m, 2H), δ 1.46 (sextet, J=7.3 Hz, 2H), δ 0.99 (t, J=7.3 Hz, 3H)

MS (CI) for $C_{20}H_{28}N_4O_2S$ m/z 389 (MH$^+$)

EXAMPLE 12

2-methyl-1-[5-(methylsulfonyl)pentyl]-1-H-imidazo[4,5-c]quinolin-4-amine

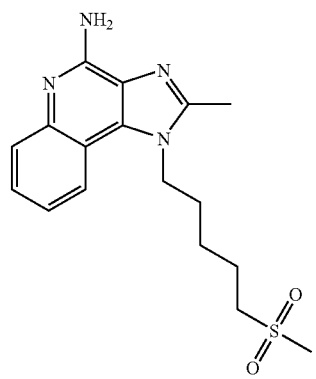

Part A

Using the general method of Example 1 Part D, N$^4$-[5-(methylthio)pentyl]quinoline-3,4-diamine (4.53 g, 16.37 mmol) was cyclized to provide 2-methyl-1-[5-(methylthio)pentyl)-1H-imidazo[4,5-c]quinoline using 1,1,1-trimethoxyethane (2.95 g, 24.6 mmol) and pyridine hydrochloride (0.1 g). The material was triturated with ethyl ether and collected by filtration to afford the product (3.78 g, 12.62 mmol) as a light brown solid which was used without further purification.

Part B

Using the general method of Example 11 Part F, 2-methyl-1-[5-(methylthio)pentyl]-1H-imidazo[4,5-c]quinoline (3.78 g, 12.62 mmol) was oxidized to 2-methyl-1-[5-(methylsulfonyl)pentyl]-1H-imidazo[4,5-c]quinoline-5N-oxide (4.38 g, 12.62 mmol) which was isolated as a tan solid and used without purification.

Part C

Using the general method of Example 3 Part B, 2-methyl-1-[5-(methylsulfonyl)pentyl]-1H-imidazo[4,5-c]quinoline-5N-oxide (4.38 g, 12.62 mmol) was aminated to provide 2-methyl-1-[5-(methylsulfonyl)pentyl]-1H-imidazo[4,5-c]quinolin-4-amine. The resulting solid was triturated with acetonitrile and collected by filtration to afford the title compound (0.8 g, 2.31 mmol) as an off-white solid, m.p. 235–240° C.

Analysis. Calculated for $C_{17}H_{22}N_4O_2S$: % C 58.94; % H, 6.40; % N, 16.17. Found: % C 58.77; % H, 6.34; % N, 16.39.

$^1$H-NMR (300 MHz, DMSO) δ 8.02 (d, J=8.3 Hz, 1H), δ 7.60 (d, J=8.3 Hz, 1H), δ 7.41 (t, J=8.3 Hz, 1H), δ 7.25 (t, J=8.3 Hz, 1H), δ 6.49 (bs, 2H), δ 4.50 (t, J=7.3 Hz, 2H), δ 3.12 (t, J=7.8 Hz, 2H), δ 2.92 (s, 3H), δ 2.61 (s, 3H), δ 1.86 (m, 2H), δ 1.74 (m, 2H), δ 1.53 (m, 2H)

MS (CI) for $C_{17}H_{22}N_4O_2S$ m/z 347 (MH$^+$), 267

EXAMPLE 13

2-ethyl-1-[5-(methylsulfonyl)pentyl]-1H-imidazo[4,5-c]quinolin-4-amine

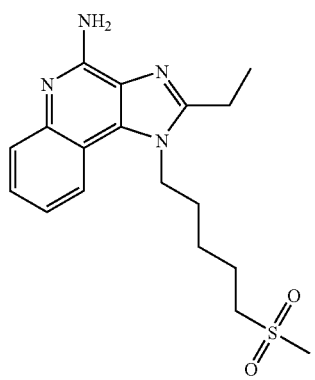

Part A

Using the general method of Example 1 Part D, N$^4$-(5-(methylthio)pentyl]quinoline-3,4-diamine (4.53 g, 16.37 mmol) was cyclized to 2-ethyl-1-[5-(methylthio)pentyl]-1H-imidazo[4,5-c]quinoline using triethyl orthopropionate (4.3 g, 24.56 mmol) and pyridine hydrochloride (0.1 g). The material was triturated with ethyl ether and collected by filtration to afford the product (3.25 g, 10.37 mmol) as an off-white powder which was used without further purification.

Part B

Using the general method of Example 11 Part F, 2-ethyl-1-[5-(methylthio)pentyl]-1H-imidazo[4,5-c]quinoline (3.25 g, 10.37 mmol) was oxidized to 2-ethyl-1-[5-(methylsulfonyl)pentyl]-1H-imidazo[4,5-c]quinoline-5N-oxide (3.75 g, 10.37 mmol) which was isolated as a tan solid and used without purification.

Part C

Using the general method of Example 3 Part B, 2-ethyl-1-[5-(methylsulfonyl)pentyl]-1H-imidazo[4,5-c]quinoline-5N-oxide (3.75 g 10.37 mmol) was aminated to provide 2-ethyl-1-[5-(methylsulfonyl)pentyl]-1H-imidazo[4,5-c] quinolin-4-amine. The resulting solid was recrystallized sequentially from ethanol and acetonitrile to afford the title compound (1.4 g, 3.88 mmol) as off white needles, m.p.189–191° C.

Analysis. Calculated for $C_{18}H_{24}N_4O_2S$: % C 59.98; % H, 6.71; % N, 15.54. Found: % C 59.71; % H, 6.68; % N, 15.64.

$^1$H-NMR (300 MHz, DMSO) δ 8.01 (d, J=8.3 Hz, 1H), δ 7.61 (d, J=8.3 Hz, 1H), δ 7.42 (t, J=8.3 Hz, 1H), δ 7.26(t, J=8.3 Hz, 1H), δ 6.45(bs, 2H), δ 4.50 (t, J=7.6 Hz, 2H), δ 3.10 (t, J=7.8 Hz, 2H), δ 2.95 (q, J=7.3 Hz, 2H), δ 2.92 (s, 3H), δ 1.85 (m, 2H), δ 1.74 (m, 2H), δ 1.55 (m, 2H), δ 1.38 (t, J=7.3 Hz, 3H)

MS (CI) for $C_{18}H_{24}N_4O_2S$ m/z 361 (MH$^+$), 281

EXAMPLE 14

1-[5-(methylsulfonyl)pentyl]-1H-imidazo[4,5-c]quinolin-4-amine

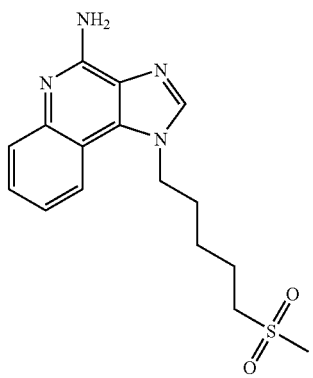

Part A

Using the general method of Example 1 Part D, N$^4$-[5-(methylthio)pentyl]quinoline-3,4-diamine (4.53 g, 16.37 mmol) was cyclized to 1-[5-(methylthio)pentyl]-1H-imidazo[4,5-c]quinoline using triethyl orthoformate (3.64 g, 24.56 mmol) and pyridine hydrochloride (0.1 g). The product (4.05 g, 14.19 mmol) was isolated as a brown oil and used without further purification.

Part B

Using the general method of Example 11 Part F, 1-[5-(methylthio)pentyl]-1H-imidazo[4,5-c]quinoline (4.05 g, 14.19 mmol) was oxidized to 1-[5-(methylsulfonyl)pentyl]-1H-imidazo[4,5-c]quinoline-5N-oxide (4.73 g, 14.19 mmol) which was isolated as a tan solid and used without further purification.

Part C

Using the general method of Example 3 Part B, 1-[5-(methylsulfonyl)pentyl]-1H-imidazo[4,5-c]quinoline-5N-oxide (4.19 aminated to provide 1-[5-(methylsulfonyl)pentyl]-1H-imidazo[4,5-c]quinolin-4-amine. The material was purified by chromatography over silica gel (95/5 dichloromethane/methanol) to afford a light yellow solid. The solid was recrystallized from dimethyl formamide to give the title compound (0.43 g, 1.29 mmol) as a light yellow, granular solid, m.p. 199–201° C.

Analysis. Calculated for $C_{16}H_{20}N_4O_2S$: % C 57.81; % H, 6.06; % N, 16.85. Found: % C 57.01; % H, 6.06; % N, 16.70.

$^1$H-NMR (300 MHz, DMSO) δ 8.20 (S, 1H), δ 8.04 (d, J=8.3 Hz, 1H), δ 7.62 (d, J=8.3 Hz, 1H), δ 7.44 (t, J=8.3 Hz, 1H), δ 7.27 (t, J=8.3 Hz, 1H), δ 6.57 (bs, 2H), δ 4.61 (t, J=6.8 Hz, 2H), δ 3.09 (t, J=7.8 Hz, 2H), δ 2.92 (s, 3H), δ 1.91 (p, J=7.6 Hz, 2H), δ 1.73 (m, 2H), δ 1.45 (m, 2H)

MS (CI) for $C_{16}H_{20}N_4O_2S$ m/z 333 (MH$^+$)

EXAMPLE 15

2-hexyl-1-[5-(methylsulfonyl)pentyl]-1H-imidazo[4,5-c]quinolin-4-amine

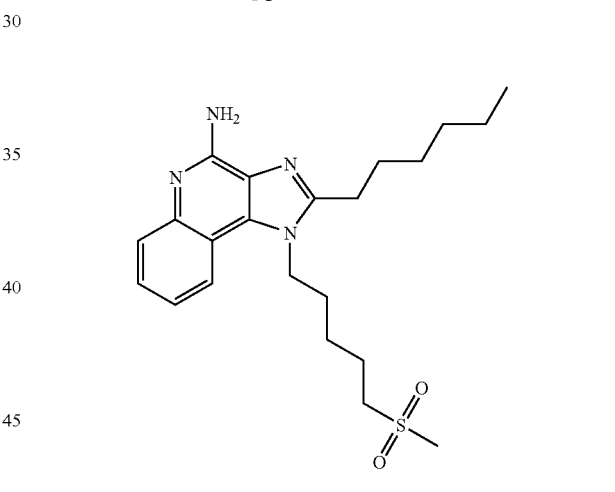

Part A

A round bottom flask was charged with a magnetic stir bar, N$^4$-[5-(methylthio)pentyl]quinoline-3,4-diamine (3.17 g, 11.46 mmol) and anhydrous pyridine (46 mL) under a nitrogen atmosphere. The resulting homogeneous solution was cooled to 0° C. in an ice-water bath. To the cooled solution was added neat heptanoyl chloride (1.87 g, 12.61 mmol). The reaction was judged to be complete after stirring at ambient temperature for 1 hour. The volatiles were removed under reduced pressure and the resulting oil was partitioned between chloroform and water. The layers were separated. The organic layer was washed with saturated aqueous sodium bicarbonate and brine, dried over anhydrous sodium sulfate, filtered and then concentrated under reduced pressure to afford N-(4-[{5-(methylthio)pentyl] amino}quinolin-3-yl)heptanamide (4.44 g, 11.46 mmol) which was isolated as a brown oil and used without further purification.

Part B

A round bottom flask was charged with a magnetic stir bar, N-(4-{[5-(methylthio)pentyl]amino}quinolin-3-yl)heptanamide (4.44 g, 11.46 mmol), pyridine hydrochloride (0.13 g, 1.15 mmol), and anhydrous pyridine (50 mL) under a nitrogen atmosphere. The reaction was judged to be complete after stirring at reflux for 1.5 hours. The solution was cooled and partitioned between ethyl acetate and water. The layers were separated. The organic layer was washed with saturated aqueous sodium bicarbonate and brine, dried over anhydrous sodium sulfate, filtered and then concentrated under reduced pressure to afford 2-hexyl-1-[5-(methylthio)pentyl]-1H-imidazo[4,5-c]quinoline (4.0 g, 10.82 mmol) as a brown oil which was used without further purification.

Part C

Using the general method of Example 11 Part F, 2-hexyl-1-[5-(methylthio)pentyl]-1H-imidazo[4,5-c]quinoline (4.0 g, 10.82 mmol) was oxidized to 2-hexyl-1-[5-(methylsulfonyl)pentyl]-1H-imidazo[4,5-c]quinoline-5N-oxide (4.52 g, 10.82 mmol) which was isolated as a tan solid and used without further purification.

Part D

Using the general method of Example 3 Part B 2-hexyl-1-[5-(methylsulfonyl)pentyl]-1H-imidazo[4,5-c]quinoline-5N-oxide (4.0 g, 10.82 mmol) was aminated to provide 2-hexyl-1-[5-(methylsulfonyl)pentyl]-1H-imidazo[4,5-c]quinolin-4-amine. The material was recrystallized from acetonitrile to afford the title compound (2.25 g, 5.40 mmol) as off-white needles, m.p. 168–171° C.

Analysis: Calculated for $C_{22}H_{32}N_4O_2S$: % C 63.43; % H, 7.74; % N, 13.45. Found: % C 63.06; % H, 7.66; % N, 13.81.

$^1$H-NMR (300 MHz, DMSO) δ 8.01 (d, J=8.3 Hz, 1H), δ 7.62 (d, J=8.3 Hz, 1H), δ 7.42 (t, J=8.3 Hz, 1H), δ 7.26 (t, J=8.3 Hz, 1H), δ 6.51 (bs, 2H), δ 4.51 (t, J=7.3 Hz, 2H), δ 3.10 (t, J=7.8 Hz, 2H), δ 2.93 (s, 3H), δ 2.93 (t, J=7.3 Hz, 2H), δ 1.71–1.87 (m, 6H), δ 1.54 (m, 2H), δ 1.44 (m, 2H), δ 1.33 (m, 4H), δ 0.89 (t, J=7.3 Hz, 3H)

MS (CI) for $C_{22}H_{32}N_4O_2S$ m/z 417 (MH$^+$), 337

EXAMPLE 16

2-(2-methoxyethyl)-1-[5-methylsulfonyl)pentyl]-1H-imidazo[4,5-c]quinolin-4-amine

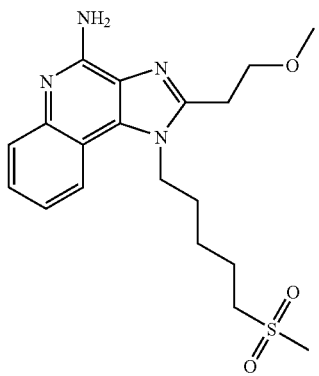

Part A

A round bottom flask was charged with a magnetic stir bar, N$^4$-[5-(methylthio)pentyl]quinoline-3,4-diamine (3.56 g, 12.93 mmol) and anhydrous pyridine (52 mL) under a nitrogen atmosphere. The resulting homogeneous solution was cooled to 0° C. in an ice-water bath. To the cooled solution was added neat 3-methoxypropionyl chloride (2.74 g, 22.36 mmol). After addition of the acid chloride, the reaction was heated to reflux for 14 hours at which time the acylated intermediate was completely consumed. The solution was cooled and then partitioned between chloroform and saturated aqueous ammonium chloride. The layers were separated. The organic layer was washed with saturated aqueous sodium bicarbonate, dried over anhydrous sodium sulfate, filtered and then concentrated under reduced pressure to afford 2-(2-methoxyethyl)-1-[5-(methylthio)pentyl]-1H-imidazo[4,5-c]quinoline (3.0 g, 8.73 mmol) which was isolated as a brown oil and used without further purification.

Part B

Using the general method of Example 11 Part F, 2-(2-methoxyethyl)-1-[5-(methylthio)pentyl]-1H-imidazo[4,5-c]quinoline (3.0 g, 8.73 mmol) was oxidized to 2-(2-methoxyethyl)-1-[5-(methylsulfonyl)pentyl]-1H-imidazo[4,5-c]quinoline-5N-oxide (3.41 g, 8.73 mmol) which was isolated as a tan solid and used without further purification.

Part C

Using the general method of Example 3 Part B, 2-(2-methoxyethyl)-1-[5-(methylsulfonyl)pentyl]-1H-imidazo[4,5-c]quinoline (3.0 g, 8.73 mmol) was aminated to provide 2-(2-methoxyethyl)-1-[5-(methylsulfonyl)pentyl]-1H-imidazo[4,5-c]quinolin-4-amine. The resulting solid was purified by chromatography over silica gel (95/5 dichloromethane/methanol) to provide a gummy solid. The solid was recrystallized from acetonitrile to give the title compound (0.54 g, 1.38 mmol) as an off-white powder, m.p. 158–160° C.

Analysis. Calculated for $C_{19}H_{26}N_4O_3S$: % C 58.44; % H, 6.71; % N, 14.35. Found: % C 58.24; % H, 6.76; % N, 14.70.

$^1$H-NMR (300 MHz, DMSO) δ 8.02 (d, J=8.3 Hz, 1H), δ 7.62 (d, J=8.3 Hz, 1H), δ 7.42 (t, J=8.3. Hz, 1H), δ 7.26 (t, J=8.3 Hz, 1H), δ 6.50 (bs, 2H), δ 4.53 (t, J=7.6 Hz, 2H), δ 3.83 (t, J=6.8 Hz, 2H), δ 3.30(s, 3H), δ 3.19(t, J=6.8 Hz, 2H), δ 3.11 (t, J=7.8 Hz, 2H), δ 2.93 (s, 3H), δ 1.85 (m, 2H), δ 1.76 (m, 2H), δ 1.57 (m, 2H)

MS (CI) for $C_{19}H_{26}N_4O_3S$ m/z 391 (MH$^+$), 359

EXAMPLE 17

2-butyl-1-[5-(methylthio)pentyl]-1H-imidazo[4,5-c]quinolin-4-amine

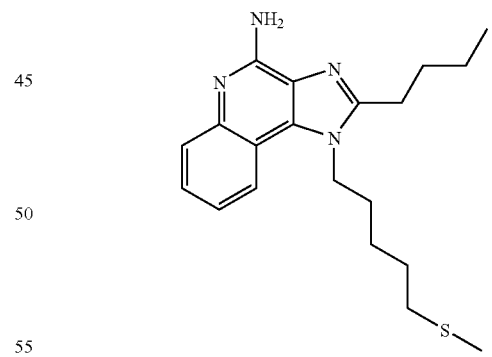

Part A

Using the general method of Example 1 Part C, N-(5-chloropentyl)-3-nitroquinolin-4-amine (2.0 g, 6.80 mmol) was reduced to provide N$^4$-(5-chloropentyl)quinoline-3,4-diamine (1.79 g, 6.80 mmol) which was isolated as a brown oil and used without further purification.

Part B

Using the general method of Example 1 Part D, N$^4$-(5-chloropentyl)quinoline-3,4-diamine (1.79 g, 6.80 mmol) was cyclized to 2-butyl-1-(5-chloropentyl)-1H-imidazo[4,5-c]quinoline using trimethyl orthovalerate (2.55 g, 15.72 mmol) and pyridine hydrochloride (0.079 g). The product (1.95 g, 5.91 mmol) was isolated as an off-white solid and used without further purification.

Part C

Using the general method of Example 1 Part E, 2-butyl-1-(5-chloropentyl)-1H-imidazo[4,5-c]quinoline (1.95 g, 5.91 mmol) was oxidized to 2-butyl-1-(5-chloropentyl)-1H-imidazo[4,5-c]quinoline-5N-oxide (2.04 g, 5.91 mmol) which was isolated as a tan solid and used without further purification.

Part D

Using the general method of Example 3 Part B, 2-butyl-1-(5-chloropentyl)-1H-imidazo[4,5-c]quinoline-5N-oxide (2.04 g, 5.91 mmol) was aminated to provide 2-butyl-1-(5-chloropentyl)-1H-imidazo[4,5-c]quinolin-4-amine. The resulting solid was recrystallized from ethanol to afford the product (0.85 g, 2.46 mmol) as a fine white powder, m.p. 144–146° C.

Analysis. Calculated for $C_{19}H_{25}ClN_4$: % C 66.17; % H, 7.31; % N, 16.24. Found: % C 66.44; % H, 7.55; % N, 16.29.

MS (CI) for $C_{19}H_{25}ClN_4$ m/z 345 (MH$^+$), 309

Part E

Using the general method of Example 6 Part B, except that the reaction temperature was lowered to 80° C., 2-butyl-1-(5-chloropentyl)-1H-imidazo[4,5-c]quinolin-4-amine (2.0 g, 5.80 mmol) was converted to 2-butyl-1-[5-(methylthio) pentyl]-1H-imidazo[4,5-c]quinolin-4-amine using sodium thiomethoxide (0.68 g, 8.70 mmol) in lieu of sodium benzenethiolate. The resulting solid was partitioned between chloroform and saturated aqueous sodium bicarbonate. The layers were separated. The organic layer was washed with brine, dried over anhydrous sodium sulfate, filtered and then concentrated under reduced pressure to afford a white solid. The material was recrystallized from acetonitrile to give the title compound (1.91 g, 5.36 mmol) as a fine white solid, m.p. 112–114° C.

Analysis. Calculated for $C_{20}H_{28}N_4S$: % C 67.38; % H, 7.92; % N, 15.71. Found: % C 67.26; % H, 8.08; % N, 15.74.

$^1$H-NMR (300 MHz, DMSO) δ 8.01 (d, J=8.3 Hz, 1H), δ 7.61 (d, J=8.3 Hz, 1H), δ 7.41 (t, J=8.3 Hz, H), δ 7.25 (t, J=8.3 Hz, 1H), δ 6.45 (bs, 2H), δ 4.50 (t, J=7.8 Hz, 2H), δ 2.92 (t, J=7.6 Hz, 2H), δ 2.46 (t, J=7.3 Hz, 2H), δ 2.01 (s, 3H), δ 1.80 (m, 4H), δ 1.42–1.61 (m, 6H), δ 0.96 (t, J=7.3 Hz, 3H)

MS (CI) for $C_{20}H_{28}N_4S$ m/z 357 (MH$^+$), 309

EXAMPLE 18

2-butyl-1-[5-(methylsulfinyl)pentyl]-1H-imidazo[4,5-c]quinolin-4-amine

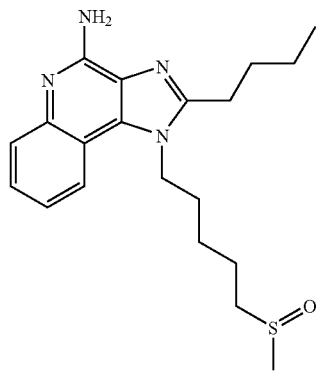

A round bottom flask was charged with a magnetic stir bar, 2butyl-1-[5-(methylthio)pentyl]-1H-imidazo[4,5-c] quinolin-4-amine (1.0 g, 2.80 mmol) and chloroform (14 mL). Solid 3-chloroperbenzoic acid (0.69 g, 3.09 mmol) was added portion wise over 5 minutes and the reaction was stirred at ambient temperature for 20 minutes at which time the starting material was completely consumed. The solution was partitioned between chloroform and saturated aqueous sodium bicarbonate. The layers were separated. The organic layer was washed with saturated aqueous sodium bicarbonate and brine, dried over anhydrous sodium sulfate filtered and then concentrated under reduced pressure to afford an off-white solid which was shown by $^1$H-NMR to be the 3-chlorobenzoic acid salt of the desired product. The solid was stirred in water and then made basic (pH 10) by addition of solid sodium carbonate. The resulting free base was collected by filtration to provide a white solid which was recrystallized from acetonitrile to give 2-butyl-1-[5-(methylsulfinyl)pentyl]-1H-imidazo[4,5-c]quinolin-4-amine (0.40 g, 1.07 mmol) as a white powder, m.p. 119–121° C.

Analysis. Calculated for $C_{20}H_{28}N_4OS$ $(H_2O)_1$: % C 61.51; % H, 7.74; % N, 14.35. Found: % C 61.64; % H, 7.82; % N, 14.32.

$^1$H-NMR (300 MHz, DMSO) δ 8.01 (d, J=8.3 Hz, 1H), δ 7.60 (d, J=8.3 Hz, 1H), δ 7.41 (t, J=8.3 Hz, 1H), δ 7.26 (t, J=8.3 Hz, 1H), δ 6.44 (bs, 2H), δ 4.51 (t, J=7.6 Hz, 2H), δ 2.92 (t, J=7.8 Hz, 2H), δ 2.57–2.74 (m, 2H), δ 2.50 (s, 3H, δ 1.80 (m, 4H), δ 1,66 (m, 2H), δ 1.55 (m, 2H), δ 1.48 (m, 2H), δ 0.96 (t, 37.3 Hz, 3H)

MS (CI) for $C_{20}H_{28}N_4OS$ $(H_2O)_1$ m/z 373 (MH$^+$), 309, 253

EXAMPLE 19

2-butyl-1-[3-(methylsulfonyl)propyl]-1H-imidazo[4,5-c]quinolin-4-amine

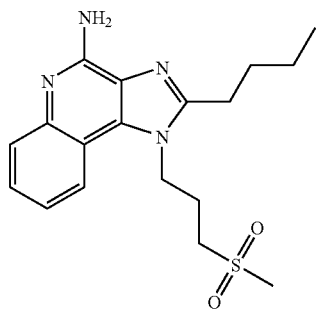

Part A

A round bottom flask was charged with a magnetic stir bar, 3-[(3-nitroquinolin-4-yl)amino]propan-1-ol (20.75 g, 83.93 mmol), thionyl chloride (15.0 g, 125.89 mmol), and dichloromethane (420 mL). The bright yellow, homogeneous solution was stirred at ambient temperature for 2 hours at which time the starting material was completely consumed. The volatiles were removed under reduced pressure and he resulting solid stirred in water (400 mL) made basic (pH 10) with solid sodium carbonate. A bright yellow solid was collected by filtration to afford N-(3-chloropropyl)-3-nitroquinolin-4-amine (21.63 g, 81.41 mmol) which was used without further purification.

Part B

Using the general method of Example 1 Part C, N-(3-chloropropyl)-3-nitroquinolin-4-amine (10.0 g, 37.63 mmol) was reduced to provide $N^4$-(3-chloropropyl)quinoline-3,4-diamine (8.87 g, 37.63 mmol) which was isolated as a brown oil and used without further purification.

Part C

Using the general method of Example 1 Part D, $N^4$-(3-chloropropyl)quinoline-3,4-diamine (8.87 g, 37.63 mmol) was cyclized to provide 2-butyl-1-(3-chloropropyl)-1H-imidazo[4,5-c]quinoline using trimethyl orthovalerate (7.33 g, 45.16 mmol) and pyridine hydrochloride (0.43 g). The resulting solid was triturated with ethyl ether and collected by filtration to afford the product (9.00 g, 29.82 mmol) as an off-white solid. The material was used without further purification.

Part D

Using the general method of Example 1 Part E, 2-butyl-1-(3-chloropropyl)-1H-imidazo[4,5-c]quinoline (9.0 g, 29.82 mmol) was oxidized to 2-butyl-1-(3-chloropropyl)-1H-imidazo[4,5-c]quinoline-5N-oxide (9.48 g, 29.82 mmol) which was isolated as a tan solid and used without purification.

Part E

Using the general-method of Example 3 Part B, 2-butyl-1-(3-chloropropyl)-1H-imidazo[4,5-c]quinoline-5N-oxide (9.48 g, 29.82 mmol) was aminated to provide 2-butyl-1-(3-chloropropyl)-1H-imidazo[4,5-c]quinolin-4-amine. The resulting solid was purified by chromatography over silica gel (95/5 dichloromethane/methanol) to provide the product (6.4 g, 20.20 mmol) as a tan solid.

Part F

Using the general method of Example 6 Part B, except that the reaction temperature was lowered to 80° C., 2-butyl-1-(3-chloropropyl)-1H-imidazo[4,5-c]quinolin-4-amine (2.0 g, 6.31 mmol) was converted to 2-butyl-1-[3-(methylthio)propyl]-1H-imidazo[4,5-c]quinolin-4-amine using sodium thiomethoxide (0.74 g, 9.47 mmol) in lieu of sodium benzenethiolate. The resulting solid was partitioned between chloroform and saturated aqueous sodium bicarbonate. The layers were separated. The organic layer was washed with brine, dried over anhydrous sodium sulfate, filtered and then concentrated under reduced pressure to afford the title compound (2.0 g, 6.09 mmol) as a white solid. The material was used without further purification.

Part G

Using the general method of Example 5 Part A, 2-butyl-1-[3-(methylthio)propyl]-1H-imidazo[4,5-c]quinolin-4-amine (2.0 g, 6.09 mmol) was oxidized to 2-butyl-1-[3-(methylsulfonyl)propyl]-1H-imidazo[4,5-c]quinolin-4-amine. The resulting solid was triturated with methanol and collected by filtration to afford the title compound (0.96 g, 2.66 mmol) as an off-white powder, m.p. 233–236° C.

Analysis. Calculated for $C_{18}H_{24}N_4O_2S$: % C 59.98; % H, 6.71; % N, 15.54. Found: % C 59.71; % H, 6.65; % N, 15.43.

$^1$H-NMR (300 MHz, DMSO) , 8.10 (d, J=8.3 Hz, 1H), δ 7.61 (d, J=8.3 Hz, 1H), δ 7.42 (t, J=8.3 Hz, 1H), δ 7.25 (t, J=8.3 Hz, 1H), δ 6.47 (bs, 2H), δ 4.66 (t, J=7.8 Hz, 2H), δ 3.40 (t, J=7.3 Hz, 2H), δ 3.01 (s, 3H), δ 2.94 (t, J=7.8 Hz, 2H), δ 2.22 (m, 2H), δ 1.80 (m, 2H), δ 1.46 (sextet, J=7.3 Hz, 2H), δ 0.96 (t, J=7.3 Hz, 3H)

MS (CI) for $C_{18}H_{24}N_4O_2S$ m/z 361 (MH$^+$), 281, 235

EXAMPLE 20

2-butyl-1-[3-(phenylsulfonyl)propyl]-1H-imidazo[4,5-c]quinolin-4-amine

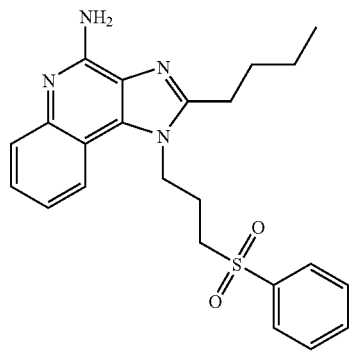

Part A

A round bottom flask was charged with a magnetic stir bar, benzenethiol (0.68 g, 6.21 mmol), sodium hydride (0.25 g, 60% dispersion, 6.21 mmol), and anhydrous dimethyl formamide (28 mL) under a nitrogen atmosphere. After the reaction mixture had stirred at ambient temperature for 30 minutes, 2-butyl-1-(3-chloropropyl)-1H-imidazo[4,5-c] quinolin-4-amine (1.64 g, 5.18 mmol) was added and the resulting cloudy solution was heated to 80° C. and maintained at 80° C. for 2.5 hours at which time the starting material was completely consumed. The hot solution was poured into rapidly stirred water (200 mL). The resulting mixture was extracted with chloroform (2×). The combined organic layers were washed with saturated aqueous sodium bicarbonate and brine, dried over anhydrous sodium sulfate, filtered and then concentrated under reduced pressure to afford a light yellow oil. The material was purified by chromatography over silica gel (95/5 dichloromethane/methanol) to provide 2-butyl-1-[3-(phenylthio)propyl]-1H-imidazo[4,5-c]quinolin-4-amine (1.38 g, 3.53 mmol) as a white solid.

Part B

Using the general method of Example 5 Part A, 2-butyl-1-[3phenylthiopropyl]-1H-imidazo[4,5-c]quinolin-4-amine (1.38 g, 3.53 mmol) was oxidized to 2-butyl-1-[3-(phenylsulfonyl)propyl]-1H-imidazo[4,5-c]quinolin-4-amine. The resulting solid was recrystallized from ethanol to provide the title compound (0.85 g, 2.01 mmol) as an off-white powder, m.p. 224–227° C.

Analysis. Calculated for $C_{23}H_{26}N_4O_2S$: % C 65.38; % H, 6.20; % N, 13.26. Found: % C 65.25; % H, 6.23; % N, 13.20.

$^1$H-NMR (300 MHz, DMSO) δ 7.96 (d, J=8.3 Hz, 1 H), δ 7.89 (m, 2H), δ 7.73 (m, 1), δ 7.63 (m, 3H), δ 7.40 (t, J=8.3 Hz, 1H), δ 7.17 (t, J=8.3 Hz, 1H), δ 6.46 (bs, 2H), δ 4.60 (t, J=7.8 Hz, 2H), δ 3.66 (t, J=7.3 Hz, 2H), 3 2.86 (t, J=7.8 Hz, 2H), δ 2.04 (m, 2H), δ 1.73 (p, J=7.6 Hz, 2H), δ 1.39 (sextet, J=7.3 Hz, 2H), δ 0.92 (t, J=7.3 Hz, 3H)

MS (CI) for $C_{23}H_{26}N_4O_2S$ m/z 423 (MH$^+$), 322, 281

Cytokine Induction Human Cells

An in vitro human blood cell system is used to assess cytokine induction. Activity is based on the measurement of interferon and tumor necrosis factor (α) (IFN and TNF, respectively) secreted into culture media as described by Testerman et. al. In "Cytokine Induction by the Immunomodulators Imiquimod and S-27609", Journal of Leukocyte Biology, 58, 365–372 (September, 1995).

Blood Cell Preparation for Culture

Whole blood from healthy human donors is collected by venipuncture into EDTA vacutainer tubes. Peripheral blood mononuclear cells (PBMCs) are separated from whole blood by density gradient centrifugation using Histopaque®-1077. The PBMCs are washed twice with Hank s Balanced Salts Solution and then are suspended at $3-4\times10^6$ cells/mL in RPMI complete. The PBMC suspension is added to 48 well flat bottom sterile tissue culture plates (Costar, Cambridge, Mass. or Becton Dickinson Labware, Lincoln Park, N.J.) containing an equal volume of RPMI complete media containing test compound.

Compound Preparation

The compounds are solubilized in dimethyl sulfoxide (DMSO). The DMSO concentration should not exceed a final concentration of 1% for addition to the culture wells. The compounds are generally tested initially at concentrations ranging from 0.12 to 30 μM. Compounds showing activity at 0.12 μM may then be tested at lower concentrations.

Incubation

The solution of test compound is added at 60 μM to the first well containing RPMI complete and serial 3 fold dilutions are made in the wells. The PBMC suspension is then added to the wells in an equal volume, bringing the test compound concentrations to the desired range (0.12 to 30 μM). The final concentration of PBMC suspension is $1.5-2\times 10^6$ cells/mL. The plates are covered with sterile plastic lids, mixed gently and then incubated for 18 to 24 hours at 37° C. in a 5% carbon dioxide atmosphere.

Separation

Following incubation the plates are centrifuged for 5–10 minutes at 1000 rpm (~200×g) at 4° C. The cell-free culture supernatant is removed with a sterile polypropylene pipet and transferred to sterile polypropylene tubes. Samples are maintained at −30 to −70° C. until analysis. The samples are analyzed for interferon (α) and for tumor necrosis factor (α) by ELISA Interferon (α) and Tumor Necrosis Factor (α) Analysis by ELISA Interferon (α) concentration is determined by ELISA using a Human Multi-Species kit from PBL Biomedical Laboratories, New Brunswick, N.J. Results are expressed in pg/mL.

Tumor necrosis factor (α) (TNF) concentration is determined using ELISA kits available from Genzyme, Cambridge, Mass.; R&D Systems, Minneapolis, Minn.; or Pharmingen, San Diego, Calif. Results are expressed in pg/mL.

The table below lists the lowest concentration found to induce interferon and the lowest concentration found to induce tumor necrosis factor for each compound. A "*" indicates that no induction was seen at any of the tested concentrations (0.12, 0.37, 1.11, 3.33, 10 and 30 μM).

| Cytokine Induction in Human Cells | | |
|---|---|---|
| Example Number | Lowest Effective Concentration (μM) | |
| | Interferon | Tumor Necrosis Factor |
| 1 | 0.12 | 0.12 |
| 2 | 0.12 | 0.37 |
| 3 | 0.04 | 0.12 |
| 4 | 0.01 | 0.01 |
| 5 | 0.01 | 0.04 |
| 6 | 3.33 | 10 |
| 7 | 3.33 | 10 |
| 8 | 10 | * |
| 9 | 3.33 | 3.33 |
| 10 | 1.11 | 1.11 |
| 11 | 0.01 | 0.12 |
| 12 | 0.12 | 10 |
| 13 | 0.12 | 3.33 |
| 14 | 3.33 | 10 |
| 15 | 0.04 | * |
| 16 | 0.01 | 0.04 |
| 17 | 0.01 | 0.04 |
| 18 | 0.01 | 0.12 |
| 19 | 0.04 | 0.37 |
| 20 | 0.04 | 0.37 |

What is claimed is:

1. A method of inducing cytokine biosynthesis in an animal comprising administering the compound 2-butyl-1-[5-(methylsulfonyl)pentyl]-1H-imidazo[4,5-c]quinolin-4-amine or a pharmaceutically acceptable salt thereof to the animal in an amount effective for cytokine induction wherein the cytokine is IFN-α and/or TNF-α.

* * * * *